(12) United States Patent
Olson

(10) Patent No.: US 10,357,322 B2
(45) Date of Patent: Jul. 23, 2019

(54) SYSTEM AND METHOD FOR CONTROLLING A REMOTE MEDICAL DEVICE GUIDANCE SYSTEM IN THREE-DIMENSIONS USING GESTURES

(71) Applicant: St. Jude Medical, Atrial Fibrillation Division, Inc., St. Paul, MN (US)

(72) Inventor: Eric S. Olson, Maplewood, MN (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 210 days.

(21) Appl. No.: 15/252,500

(22) Filed: Aug. 31, 2016

(65) Prior Publication Data

US 2017/0049524 A1    Feb. 23, 2017

Related U.S. Application Data

(63) Continuation-in-part of application No. 13/637,401, filed on Dec. 6, 2012, now Pat. No. 9,888,973, and a continuation of application No. 13/692,356, filed on Dec. 3, 2012, now Pat. No. 9,439,736, which is a continuation-in-part of application No. 13/208,924, filed as application No. PCT/US2011/030764 on Mar. 31, 2011, now Pat. No. 9,330,497, and a continuation of application No. 12/507,175, filed on Jul. 22, 2009, now Pat. No. 8,390,438.

(Continued)

(51) Int. Cl.
*A61B 34/00* (2016.01)
*A61B 5/00* (2006.01)
(Continued)

(52) U.S. Cl.
CPC .............. *A61B 34/74* (2016.02); *A61B 5/042* (2013.01); *A61B 34/25* (2016.02); *A61B 34/76* (2016.02);
(Continued)

(58) Field of Classification Search
CPC ... G06T 19/003; G06T 2210/41; G06F 3/014; G06F 3/01–011; G06F 3/03545;
(Continued)

(56) References Cited

U.S. PATENT DOCUMENTS 3,091,130 A    5/1963    Payerle et al.
3,605,725 A    9/1971    Bentov
(Continued)

FOREIGN PATENT DOCUMENTS

EP    0151479    8/1985
EP    0904796    3/1999
(Continued)

OTHER PUBLICATIONS

Title: Supplemental European Search Report Citation: EP Application No. 11763450.1 Publication Date: Oct. 29, 2014 9 pages.
(Continued)

*Primary Examiner* — Bao Long T Nguyen
(74) *Attorney, Agent, or Firm* — Dykema Gossett PLLC

(57) ABSTRACT

A system for enabling a user to remotely control a robotic medical device system includes a motion capture apparatus to capture motion of a user in a sensing volume and generate indicative output data. The system includes a control unit configured to execute gesture recognition logic that recognizes a user gesture based on analysis of the indicative output data. The control unit executes interpreter logic that is configured to translate the recognized user gesture into a corresponding robotic medical device control command configured to control an aspect of the operation of the robotic medical device system.

19 Claims, 21 Drawing Sheets

Related U.S. Application Data

(60) Provisional application No. 61/319,795, filed on Mar. 31, 2010.

(51) Int. Cl.
*G06T 19/00* (2011.01)
*G06F 3/01* (2006.01)
*G06F 3/0354* (2013.01)
*A61B 5/042* (2006.01)
*B25J 9/16* (2006.01)
*G06K 9/00* (2006.01)
*A61B 34/30* (2016.01)

(52) U.S. Cl.
CPC .............. *B25J 9/161* (2013.01); *G06F 3/014* (2013.01); *G06F 3/017* (2013.01); *G06F 3/03545* (2013.01); *G06K 9/00335* (2013.01); *G06T 19/003* (2013.01); *A61B 34/30* (2016.02); *A61B 2034/258* (2016.02); *A61B 2034/741* (2016.02); *G06T 2210/41* (2013.01)

(58) Field of Classification Search
CPC ......... G06F 3/017; A61B 5/042; A61B 19/56; A61B 2019/223; A61B 2019/5287; A61B 2017/00207; A61B 2017/00017; A61B 2017/00212; A61B 34/74; A61B 34/25; A61B 34/76; A61B 2034/258; A61B 34/30; A61B 2034/741; A61B 2034/2068; A61B 34/35; A61B 34/37; A61B 2034/301; A63F 13/06; A63F 13/212–213; B25J 1/00; B25J 3/00; B25J 9/0081; B25J 13/087; B25J 9/161; G05B 19/42; G05B 19/427; G05B 2219/40399; G05B 2219/40403; G05B 2219/40405; G05B 2219/32014; G05B 2219/35444; G05B 2219/23021; Y10S 901/02–03; Y10S 901/46–47; Y10S 901/50; G06K 9/00335
USPC ......... 700/250, 253, 257–259, 264; 901/2–3, 901/46–47, 50; 318/568.11, 568.13, 318/568.16, 568.23, 568.25; 715/863
See application file for complete search history.

(56) References Cited

U.S. PATENT DOCUMENTS

| | | |
|---|---|---|
| 3,893,449 A | 7/1975 | Lee et al. |
| 4,160,508 A | 7/1979 | Frosch et al. |
| 4,348,556 A | 9/1982 | Gettig et al. |
| 4,393,728 A | 7/1983 | Larson et al. |
| 4,494,417 A | 1/1985 | Larson |
| 4,543,090 A | 9/1985 | McCoy |
| 4,758,222 A | 7/1988 | McCoy |
| 4,784,042 A | 11/1988 | Paynter |
| 4,802,487 A | 2/1989 | Martin |
| 4,884,557 A | 12/1989 | Takehana |
| 4,962,448 A | 10/1990 | DeMaio |
| 4,974,151 A | 11/1990 | Advani et al. |
| 5,078,140 A | 1/1992 | Kwoh |
| 5,107,080 A | 4/1992 | Rosen |
| 5,170,817 A | 12/1992 | Sunderland |
| 5,238,005 A | 8/1993 | Imran |
| 5,298,930 A | 3/1994 | Asakura |
| 5,303,148 A | 4/1994 | Mattson et al. |
| 5,318,525 A | 6/1994 | West |
| 5,339,799 A | 8/1994 | Kami et al. |
| 5,396,266 A | 3/1995 | Brlmhall et al. |
| 5,410,638 A | 4/1995 | Colgate et al. |
| 5,441,483 A | 8/1995 | Avitall |
| 5,449,345 A | 9/1995 | Taylor |
| 5,520,644 A | 5/1996 | Imran |
| 5,533,967 A | 7/1996 | Imran |
| 5,545,200 A | 8/1996 | West |
| 5,579,442 A | 11/1996 | Kimoto |
| 5,607,158 A | 3/1997 | Chan |
| 5,607,462 A | 3/1997 | Imran |
| 5,623,582 A | 4/1997 | Rosenberg |
| 5,630,783 A | 5/1997 | Steinberg |
| 5,656,903 A * | 8/1997 | Shui .......................... B25J 3/04 318/568.1 |
| 5,661,253 A | 8/1997 | Aoki |
| 5,706,827 A | 1/1998 | Ehr |
| 5,784,542 A | 7/1998 | Ohm |
| 5,791,908 A | 8/1998 | Gillio |
| 5,800,178 A | 9/1998 | Gillio |
| 5,807,377 A | 9/1998 | Madhani |
| 5,808,665 A | 9/1998 | Green |
| 5,828,813 A | 10/1998 | Ohm |
| 5,854,622 A | 12/1998 | Brannon |
| 5,861,024 A | 1/1999 | Rashidi |
| 5,876,325 A | 3/1999 | Mizuno et al. |
| 5,897,488 A | 4/1999 | Ueda |
| 5,913,820 A | 6/1999 | Bladen et al. |
| 6,040,758 A | 3/2000 | Sedor |
| 6,063,095 A | 5/2000 | Wang |
| 6,113,395 A | 9/2000 | Hon |
| 6,201,196 B1 | 3/2001 | Wergen |
| 6,233,476 B1 | 5/2001 | Strommer et al. |
| 6,233,504 B1 | 5/2001 | Das et al. |
| 6,290,683 B1 | 9/2001 | Erez |
| 6,348,911 B1 | 2/2002 | Rosenberg |
| 6,358,207 B1 | 3/2002 | Lathbury et al. |
| 6,385,509 B2 | 5/2002 | Das et al. |
| 6,396,232 B2 | 5/2002 | Haanpaa |
| 6,432,112 B2 | 8/2002 | Brock |
| 6,498,944 B1 | 12/2002 | Ben-Haim et al. |
| 6,500,167 B1 | 12/2002 | Webster |
| 6,522,141 B2 | 2/2003 | Debbins et al. |
| 6,540,685 B1 | 4/2003 | Rhoads et al. |
| 6,671,533 B2 | 12/2003 | Chen et al. |
| 6,690,963 B2 | 2/2004 | Ben-Haim et al. |
| 6,709,667 B1 | 3/2004 | Lowe |
| 6,785,358 B2 | 8/2004 | Johnson |
| 6,788,967 B2 | 9/2004 | Ben-Haim et al. |
| 6,850,252 B1 | 2/2005 | Hoffberg |
| 6,869,390 B2 | 3/2005 | Elliott |
| 6,869,396 B2 | 3/2005 | Belson |
| 6,968,223 B2 | 11/2005 | Hanover |
| 6,985,865 B1 | 1/2006 | Packingham |
| 7,016,469 B2 | 3/2006 | Johnson et al. |
| 7,193,521 B2 | 3/2007 | Moberg |
| 7,197,354 B2 | 3/2007 | Sobe |
| 7,199,790 B2 | 4/2007 | Rosenberg |
| 7,247,139 B2 | 7/2007 | Yudkovitch et al. |
| 7,263,397 B2 | 8/2007 | Hauck |
| 7,276,044 B2 | 10/2007 | Ferry |
| 7,386,339 B2 | 6/2008 | Strommer et al. |
| 7,405,280 B2 | 12/2008 | Dudney et al. |
| 7,465,288 B2 | 12/2008 | Dudney et al. |
| 7,672,849 B2 | 3/2010 | Yudkovitch et al. |
| 7,698,966 B2 | 4/2010 | Gosselin |
| 7,742,803 B2 | 6/2010 | Viswanathan et al. |
| 7,850,642 B2 | 12/2010 | Moll |
| 7,880,717 B2 | 2/2011 | Berkley et al. |
| 7,885,707 B2 | 2/2011 | Hauck |
| 7,945,546 B2 | 5/2011 | Bliss et al. |
| 7,963,288 B2 | 6/2011 | Rosenberg et al. |
| 8,164,573 B2 | 4/2012 | DaCosta et al. |
| 8,317,744 B2 | 11/2012 | Kirschenman |
| 8,317,745 B2 | 11/2012 | Kirschenman |
| 8,332,072 B1 | 12/2012 | Schaible et al. |
| 8,390,438 B2 | 3/2013 | Olson |
| 8,416,203 B2 | 4/2013 | Tsui |
| 8,521,331 B2 * | 8/2013 | Itkowitz .............. A61B 19/2203 606/1 |
| 8,560,118 B2 | 10/2013 | Greer et al. |
| 8,926,511 B2 | 1/2015 | Bar-Tar |
| 9,052,710 B1 * | 6/2015 | Farwell ................ G05B 19/423 |
| 2001/0018591 A1 | 8/2001 | Brock |
| 2001/0025183 A1 | 9/2001 | Shahidi |

(56) References Cited

U.S. PATENT DOCUMENTS

| | | |
|---|---|---|
| 2002/0065485 A1 | 5/2002 | DuBois et al. |
| 2002/0068868 A1 | 6/2002 | Thompson et al. |
| 2002/0072704 A1 | 6/2002 | Mansouri-Ruiz |
| 2002/0087048 A1 | 7/2002 | Brock |
| 2002/0184055 A1 | 12/2002 | Naghavi et al. |
| 2003/0018232 A1 | 1/2003 | Elliott |
| 2003/0050733 A1 | 3/2003 | Wang et al. |
| 2003/0114962 A1 | 6/2003 | Niemeyer |
| 2003/0121382 A1 | 7/2003 | Morson |
| 2004/0050247 A1 | 3/2004 | Topping |
| 2004/0068173 A1 | 4/2004 | Viswanathan |
| 2004/0133189 A1 | 7/2004 | Sakurai |
| 2004/0138530 A1 | 7/2004 | Kawai et al. |
| 2004/0146388 A1 | 7/2004 | Khajepour et al. |
| 2004/0193239 A1 | 9/2004 | Falwell et al. |
| 2004/0223636 A1 | 11/2004 | Edic |
| 2004/0243147 A1 | 12/2004 | Lipow |
| 2005/0038333 A1 | 2/2005 | Sra |
| 2005/0075538 A1 | 4/2005 | Banik |
| 2005/0172405 A1 | 8/2005 | Menkedick et al. |
| 2005/0203382 A1 | 9/2005 | Govari |
| 2005/0222554 A1 | 10/2005 | Wallace |
| 2005/0234293 A1 | 10/2005 | Yamamoto et al. |
| 2005/0234320 A1 | 10/2005 | Balasubramanian |
| 2006/0052664 A1 | 3/2006 | Julian |
| 2006/0089637 A1 | 4/2006 | Werneth et al. |
| 2006/0137476 A1 | 6/2006 | Bull |
| 2006/0155321 A1 | 7/2006 | Bressler et al. |
| 2006/0276775 A1 | 12/2006 | Rosenberg et al. |
| 2007/0016008 A1* | 1/2007 | Schoenefeld ......... A61B 90/36 600/424 |
| 2007/0022384 A1 | 1/2007 | Abbott et al. |
| 2007/0043338 A1 | 2/2007 | Moll et al. |
| 2007/0060833 A1 | 3/2007 | Hauck |
| 2007/0073137 A1 | 3/2007 | Schoenefeld |
| 2007/0100254 A1 | 5/2007 | Murakami et al. |
| 2007/0120512 A1 | 5/2007 | Albu-Schaffer et al. |
| 2007/0135803 A1 | 6/2007 | Belson |
| 2007/0142726 A1 | 6/2007 | Carney |
| 2007/0172803 A1 | 7/2007 | Hannaford et al. |
| 2007/0185404 A1 | 8/2007 | Hauck et al. |
| 2007/0185485 A1 | 8/2007 | Hauck |
| 2007/0185486 A1 | 8/2007 | Hauck |
| 2007/0197896 A1 | 8/2007 | Moll et al. |
| 2007/0197939 A1 | 8/2007 | Wallace |
| 2007/0198008 A1 | 8/2007 | Hauck et al. |
| 2007/0233044 A1 | 10/2007 | Wallace |
| 2007/0233045 A1 | 10/2007 | Weitzner |
| 2007/0257821 A1 | 11/2007 | Son et al. |
| 2007/0268269 A1 | 11/2007 | Chang et al. |
| 2007/0270685 A1 | 11/2007 | Kang |
| 2007/0276214 A1 | 11/2007 | Dachille |
| 2007/0298877 A1 | 12/2007 | Rosenberg et al. |
| 2008/0009791 A1 | 1/2008 | Cohen et al. |
| 2008/0013809 A1 | 1/2008 | Zhu |
| 2008/0112842 A1 | 5/2008 | Edwards |
| 2008/0201847 A1 | 8/2008 | Menkedick |
| 2008/0297490 A1 | 12/2008 | Adkins |
| 2008/0312536 A1 | 12/2008 | Dala-Krishna |
| 2009/0012533 A1 | 1/2009 | Barbagli |
| 2009/0033623 A1 | 2/2009 | Lin |
| 2009/0061928 A1 | 3/2009 | Lee et al. |
| 2009/0062602 A1* | 3/2009 | Rosenberg ........ A61M 25/0138 600/101 |
| 2009/0123111 A1 | 5/2009 | Udd |
| 2009/0137952 A1 | 5/2009 | Ramamurthy et al. |
| 2009/0138280 A1 | 5/2009 | Morita |
| 2009/0177454 A1 | 7/2009 | Bronstein |
| 2009/0192519 A1 | 7/2009 | Omori et al. |
| 2009/0195514 A1 | 8/2009 | Glynn et al. |
| 2009/0247943 A1 | 10/2009 | Kirschenman et al. |
| 2009/0247993 A1 | 10/2009 | Kirschenman et al. |
| 2009/0248042 A1 | 10/2009 | Kirschenman |
| 2009/0264156 A1 | 10/2009 | Burghardt et al. |
| 2009/0322697 A1 | 12/2009 | Cao |
| 2009/0326406 A1* | 12/2009 | Tan ................ G06F 3/015 600/546 |
| 2009/0327888 A1 | 12/2009 | Whytock |
| 2010/0053085 A1 | 3/2010 | Hall |
| 2010/0066676 A1* | 3/2010 | Kramer ............. G06F 3/017 345/158 |
| 2010/0073150 A1 | 3/2010 | Olson et al. |
| 2010/0079386 A1 | 4/2010 | Scott et al. |
| 2010/0082039 A1 | 4/2010 | Mohr et al. |
| 2010/0103127 A1 | 4/2010 | Park et al. |
| 2010/0131482 A1 | 5/2010 | Linthicum |
| 2010/0256558 A1 | 10/2010 | Olson et al. |
| 2010/0268067 A1 | 10/2010 | Razzaque et al. |
| 2010/0314031 A1 | 12/2010 | Heideman et al. |
| 2011/0015569 A1 | 1/2011 | Kirschenman et al. |
| 2011/0040547 A1 | 2/2011 | Gerber et al. |
| 2011/0128555 A1 | 6/2011 | Rotschild et al. |
| 2011/0137156 A1 | 6/2011 | Razzaque et al. |
| 2011/0152882 A1 | 6/2011 | Wenderow et al. |
| 2011/0289441 A1 | 11/2011 | Venon et al. |
| 2011/0306986 A1 | 12/2011 | Lee et al. |
| 2012/0071891 A1 | 3/2012 | Itkowitz et al. |
| 2012/0133601 A1 | 5/2012 | Marshall et al. |
| 2012/0172702 A1 | 7/2012 | Koyrakh et al. |
| 2012/0277663 A1 | 11/2012 | Millman et al. |
| 2013/0006268 A1 | 1/2013 | Swarup et al. |
| 2013/0154913 A1 | 6/2013 | Genc et al. |
| 2013/0165854 A1 | 6/2013 | Sandhu et al. |
| 2013/0176220 A1 | 7/2013 | Merschon et al. |
| 2013/0179162 A1 | 7/2013 | Merschon et al. |

FOREIGN PATENT DOCUMENTS

| | | |
|---|---|---|
| GB | 2211280 | 6/1989 |
| GB | 2397177 | 7/2007 |
| JP | S60221280 | 11/1985 |
| JP | H06344285 | 12/1994 |
| JP | H8-280709 | 10/1996 |
| JP | H10216238 | 8/1998 |
| JP | 2003024336 | 1/2003 |
| JP | 2007-325936 | 12/2007 |
| WO | 9320535 | 10/1993 |
| WO | 1996/039944 | 12/1996 |
| WO | 9639944 | 12/1996 |
| WO | 2003049596 | 6/2003 |
| WO | 2006/120666 | 11/2006 |
| WO | 2007056590 | 5/2007 |
| WO | 2007/088208 | 8/2007 |
| WO | 2007/098494 | 8/2007 |
| WO | 2007/120329 | 10/2007 |
| WO | 2007136803 | 11/2007 |
| WO | 2007/146325 | 12/2007 |
| WO | 2007143859 | 12/2007 |
| WO | 2008045831 | 4/2008 |
| WO | 2008101228 | 8/2008 |
| WO | 2008103212 | 8/2008 |
| WO | 2009/120982 | 10/2009 |
| WO | 2009/120982 A2 | 10/2009 |
| WO | 2009/120992 | 10/2009 |
| WO | 2009120940 | 10/2009 |
| WO | 2009120992 | 10/2009 |
| WO | 2010025338 | 3/2010 |
| WO | 2010059179 | 5/2010 |
| WO | 2010068783 | 6/2010 |
| WO | 2010107916 | 9/2010 |
| WO | 2013/101273 A1 | 7/2013 |

OTHER PUBLICATIONS

Title: International Search Report Citation: PCT Application No. PCT/US2011/030656 Publication Date: Jun. 13, 2011 8 pages.

Title: Emotiv—Brain Computer interface Technology (online) Citation: <URL: http://www.emotiv.com> Publication Date: Aug. 11, 2011 3 pages.

Title: Supplemental European Search Report Citation: EP Application No. 09726364.4 Publication Date: Jan. 22, 2013 7 pages.

Title: Supplemental European Search Report Citation: EP Application No. 09723739.0 Publication Date: Jul. 10, 2012 6 pages.

(56) References Cited

OTHER PUBLICATIONS

Title: Supplemental European Search Report Citation: EP Application No. 09724550.0 Publication Date: Jul. 10, 2012 6 pages.
Title: International Search Report Citation: PCT Application No. PCT/US2009/058121 Publication Date: Nov. 19, 2009 2 pages.
Title: International Search Report Citation: PCT Application No. PCT/US2009/038536 Publication Date: May 28, 2009 2 pages.
Title: International Search Report Citation: PCT Application No. PCT/US2009/038534 Publication Date: May 27, 2009 2 pages.
Supplementary European Search Report for EP Application No. 11763410.5, dated Jun. 10, 2015. 7 pages.
Title: International Search Report Citation: PCT Application No. PCT/US2009/038597 Publication Date: May 18, 2009 2 pages.
Title: International Search Report Citation: PCT Application No. PCT/US2009/038618 Publication Date: May 22, 2009 2 pages.
International Search Report for PCT Application No. PCT/US2009/069712, dated Feb. 25, 2010; 10 pgs.
Supplementary European Search Report for EP Application No. 09725131.8, dated Feb. 20, 2013. 7 pgs.
Title: International Search Report Citation: PCT Application No. PCT/US2009/038525 Publication Date: May 27, 2009 2 pages.
Title: International Search Report Citation: PCT Application No. PCT/US2009/038531 Publication Date: May 19, 2009 3 pages.
Title: International Search Report Citation: PCT Application No. PCT/US2009/038533 Publication Date: Jun. 17, 2009 2 pages.
Title: The Aurora Electromagnetic Tracking System, Aurora Electromagnetic Measurement System—3D Tracking for Medical Guidance Citation: Northern Digital, Inc. <URL: http://www.ndigital.com/medical/aurora.pho?act=print> Publication Date: (actual publication date unknown) 3 pages.
Title: Apple Wins Strategic Multitouch and Music Tempo Workout Patents Citation: Patently Apple <URL: http://www.patentlyapple.com/patently-apple/2010/04/apple-wins-strategic-multitouch-music-tempo-workout-patents.html> Publication Date: (actual publication date unknown) 5 pages.
Polaris Family of Optical Tracking Systems, Polaris Vicra & Spectra-Optical Measurement Systems for Medical Citation: Northern Digital Inc. <URL: http://www.ndigital.com/medical/polarisfamily.php?act=print> Publication Date: (actual publication date unknown) 5 pages.
Author: LaBelle, Kathryn Title: Evaluation of Kinect Joint Tracking for Clinical and In-Home Stroke Rehabilitation Tools Citation: <http://netscale.cse.nd.edu/twiki/pub/Edu/KinectRehabilitation/Eval_of_Kinect_for_Rehab.pdf> Publication Date: Dec. 2011 67 pages.
Author: Padoy, Nicolas Title: Needle Insertion Revisted (telesurgery in depth), (online) Citation: The John Hopkins University <URL: http://www.youtube.com/watch?v=YsY_A0kLh-g> Publication Date: Jan. 2011 25 pages.
Title: Emotiv EPOC Software Development Kit—EPOC neuroheadset (online) Citation: <URL: http://www.emotiv.com/store/hardware/epoc/bci/epoc-neuroheadseU> Publication Date: (actual publication date unknown) 2 pages.
Title: Wii Remote—Wkipedia, the free encyclopedia (online) Citation: <URL: http://en.wikipedia.org/wiki/Wii_Remote> Publication Date: (actual publication date unknown) 17 pages.
Title: About the Kinect for Windows SDK—Microsoft Research (online) Citation: <URL: http://research.microsoft.com/en-us/um/redmond/projects/kinectsdk/about.aspx> Publication Date: (actual publication date unknown) 2 pages.
Title: Kinect—Wikipedia, the free encyclopedia (online) Citation: <URL: http://en.wikipedia.org/wiki/Kinect> Publication Date: (actual publication date unknown) 15 pages.
Title: International Search Report & Written Opinion Citation: PCT/US2012/031008 Publication Date: Jul. 20, 2012 10 pages.
Title: International Search Report and Written Opinion Citation : PCT/US2011/030764 Publication Date: Jun. 15, 2011 8 pages.
Ghobadi, et al. "Real Time Hand Based Robot Control Using Multimodal Images", IAENG International Journal of Computer Sciences, 35:4, IJCS_35_4_08; Nov. 20, 2008. 6 pgs.
Robot.pdf (Robot—Definition Robot at Dictionary.com, Oct. 27, 2015, http://dictionary.reference.com/browse/robot, pp. 1-5).

\* cited by examiner

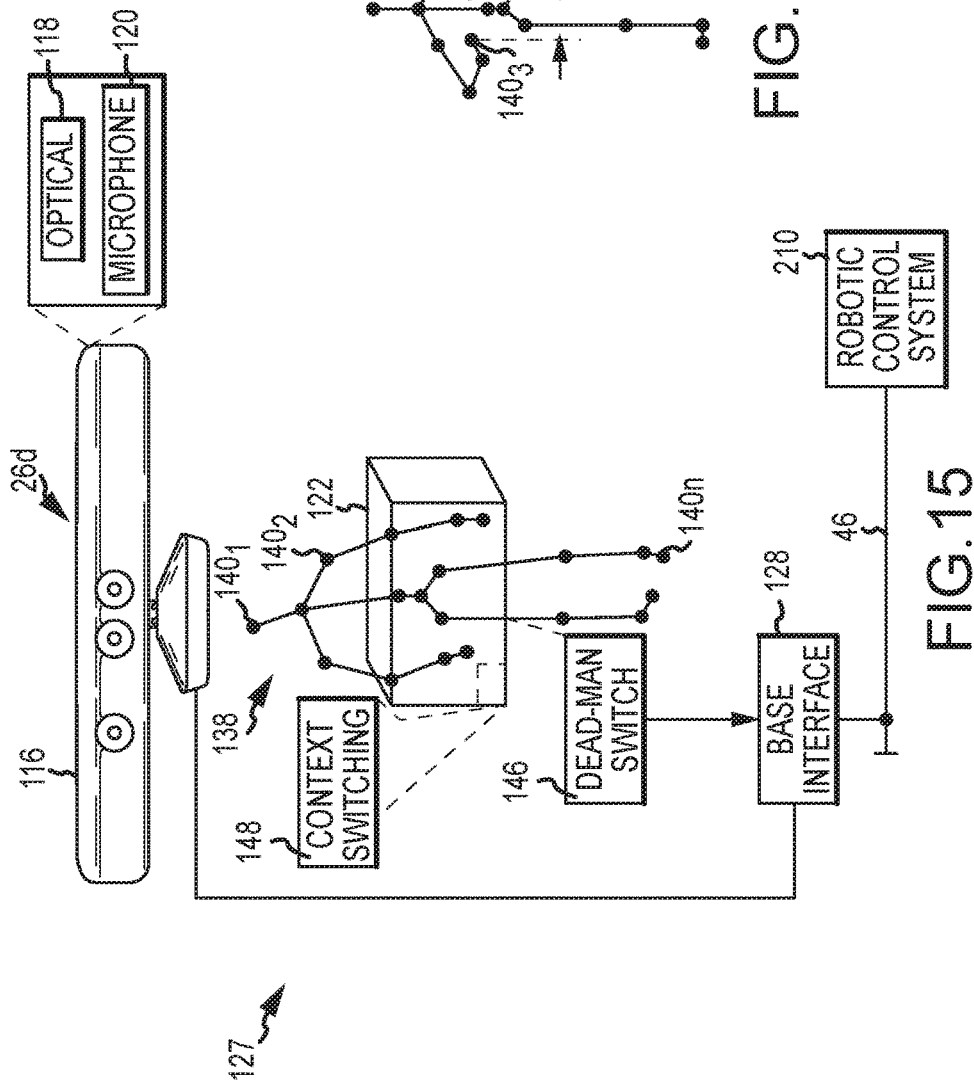

SYSTEM AND METHOD FOR CONTROLLING A REMOTE MEDICAL DEVICE GUIDANCE SYSTEM IN THREE-DIMENSIONS USING GESTURES

CROSS-REFERENCES TO RELATED APPLICATIONS

This application is a continuation of U.S. application Ser. No. 13/692,356, filed 3 Dec. 2012 (the '356 application), which is a continuation-in-part of U.S. application Ser. No. 13/208,924, filed 12 Aug. 2011, now U.S. Pat. No. 9,330,497 (the '924 application). This application is also a continuation-in-part of U.S. application Ser. No. 12/507,175, filed 22 Jul. 2009, now U.S. Pat. No. 8,390,438 (the '175 application). This application is also a continuation-in-part of U.S. application Ser. No. 13/637,401, filed 26 Sep. 2012, now pending (the '401 application), which is the national stage of international application no. PCT/US11/30764, with an international filing date of 31 Mar. 2011 (the '764 application), which claims priority to U.S. provisional application No. 61/319,795, filed 31 Mar. 2010 (the '795 application). The '356, '924 application, the '175 application, the '401 application, the '764 application, and the '795 application are all hereby incorporated by reference as though fully set forth herein.

BACKGROUND a. Technical Field

The instant disclosure relates generally to electrophysiology lab integration, and more particularly to user interfaces and devices therefore for robotic control of electrophysiology lab diagnostic and therapeutic equipment.

b. Background Art

It is known to provide an electrophysiology lab in a medical facility. Such a lab may have use of a wide variety of diagnostic and therapeutic equipment useful in rendering medical service to a patient, such as imaging systems (e.g., fluoroscopy, intracardiac echocardiography, etc.), an electro-anatomic visualization, mapping and navigation system, ablation energy sources (e.g., radio frequency (RF) ablation generator), a recording system (e.g., for ECG, cardiac signals, etc.), a cardiac stimulator and the like. In a typical configuration, as seen by reference to FIG. 1, a procedure room 10 (i.e., a sterile environment) may have an associated control area or room 12, which is commonly outfitted with one or more control stations $14_1$, $14_2$, . . . $14_n$ that are operated by one or more control technicians. Each control station may include a respective display monitor, keyboard and mouse for use by the technician. Depending on the lab setup, the control station(s) may be across the room, or outside of the procedure room 10 completely, perhaps configured with a common window to allow the technician(s) to observe the procedure room through the window. These control station(s) allow access to and may be used to control the diagnostic and therapeutic equipment mentioned above.

In conventional practice, an electrophysiology (EP) physician 16 is scrubbed into a sterile procedure and typically manipulates one or more catheters (not shown) in a sterile drape covered body of the patient 18. The physician's sterile gloved hands are typically engaged with the catheter handle and shaft next to the patient and he or she is therefore unable to directly make changes himself to any of the EP systems. The procedure room 10 typically includes one or more monitors (e.g., an integrated multi-display monitor 20 is shown) arranged so that the physician 16 can see the monitor 20 on which is displayed various patient information being produced by the diagnostic and therapeutic equipment mentioned above. In FIG. 1, multiple applications, for example, an electro-anatomic mapping application (e.g., EnSite™ Velocity™) and an EP signal acquisition and recording application, direct a visual output to a respective display area of monitor 20. When changes to an application are needed, the physician 16 verbalizes such commands to the control technicians in the control area/room 12 who are working at the various control stations $14_1$, $14_2$, . . . $14_n$. The multiple technicians at multiple control stations use multiple keyboard/mouse sets to control the multiple applications. The verbal commands between the physician and the technician occur throughout the procedure.

For example, the EP physician 16 can verbally communicate (i.e., to the control technician—a mapping system operator) the desired view of the map to be displayed, when to collect points, when to separate anatomic locations, and other details of creating and viewing an anatomic map. The EP physician 16 can also communicate which signal traces to show, the desired amplitude, when to drop a lesion marker, and when to record a segment, to name a few. Where the technician is in a separate room, communication can be facilitated using radio.

While some commands are straightforward, for example, "LAO View", "record that" and "stop pacing", other commands are not as easy to clearly communicate. For example, how much rotation of a model the command "rotate a little to the right" means can be different as between the physician and the technician. This type of command therefore involves a question of degree. Also, depending on the physician-technician relationship, other requests related to the mapping system views and setup can be misinterpreted. For example, a request to "rotate right" may mean to rotate the model right (i.e., rotate view left) when originating from one physician but can alternatively mean rotate view right (i.e., rotate model left) when coming from another physician. This type of command therefore involves physician-technician agreement as to convention. Furthermore, implementation of requests for event markers, segment recordings, lesion markers and the like can be delayed by the time it takes the technician to hear, understand and act on a physician's command. Ambient discussions and/or equipment noise in and around the EP lab can increase this delay.

Certain catheter procedures can be performed through the use of a remote catheter guidance system (RCGS), which employs robotically-controlled movement of the catheter. The robotic control can receive input command through a user interface that can include a joystick, mouse or the like. However, there is a need for an improved user interface to control an RCGS.

The foregoing discussion is intended only to illustrate the present field and should not be taken as a disavowal of claim scope.

SUMMARY

One advantage of the methods and apparatuses described, depicted and claimed herein is that they provide an EP physician or other user with the capability of directly controlling a robotic catheter system. In an embodiment, a system for enabling a user to remotely control a robotic catheter system includes a motion capture apparatus and an electronic control unit. The motion capture apparatus is configured to capture motion of a user in a sensing volume and generate output data indicative of the captured user motion. The electronic control unit includes one or more processors and memory. The system further includes gesture recognition logic stored in the memory and configured to execute on the one or more processors. The gesture recognition logic is configured to recognize a user gesture based on the output data generated by the motion capture apparatus. The system further includes interpreter logic stored in the memory and configured to be executed by the one or more processors. The interpreter logic is configured to translate the recognized user gestures to a corresponding robotic catheter control command wherein the command is configured to control an aspect of the operation of the robotic catheter system. The electronic control unit is configured to communicate the command to the robotic catheter system.

In an embodiment, the motion capture apparatus is configured to acquire imaging of the movements of the user. For example only, the motion capture apparatus provides the capability of receiving input by way of physician gestures (e.g., hand, arm, leg, trunk, facial, etc.).

In an embodiment, the user motion data includes fiducial point tracking data, and wherein the gesture recognition logic is configured to identify a start pose based on fiducial point tracking data, record the motion a predetermined plurality of fiducial points after the start pose until an end pose is identified based on the fiducial point tracking data, compare the recorded motion of the predetermined plurality of fiducial points with a plurality of predefined gestures, and output the user gesture when the recorded motion matches one of the plurality of gestures.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 15 is a diagrammatic and block diagram of an embodiment of a system for enabling a user to control a robotic catheter system.

FIGS. 16A-16B are schematic, skeleton representations of a user showing, respectively, a distance metric between fiducial points and rotation metric relative to a fiducial point.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
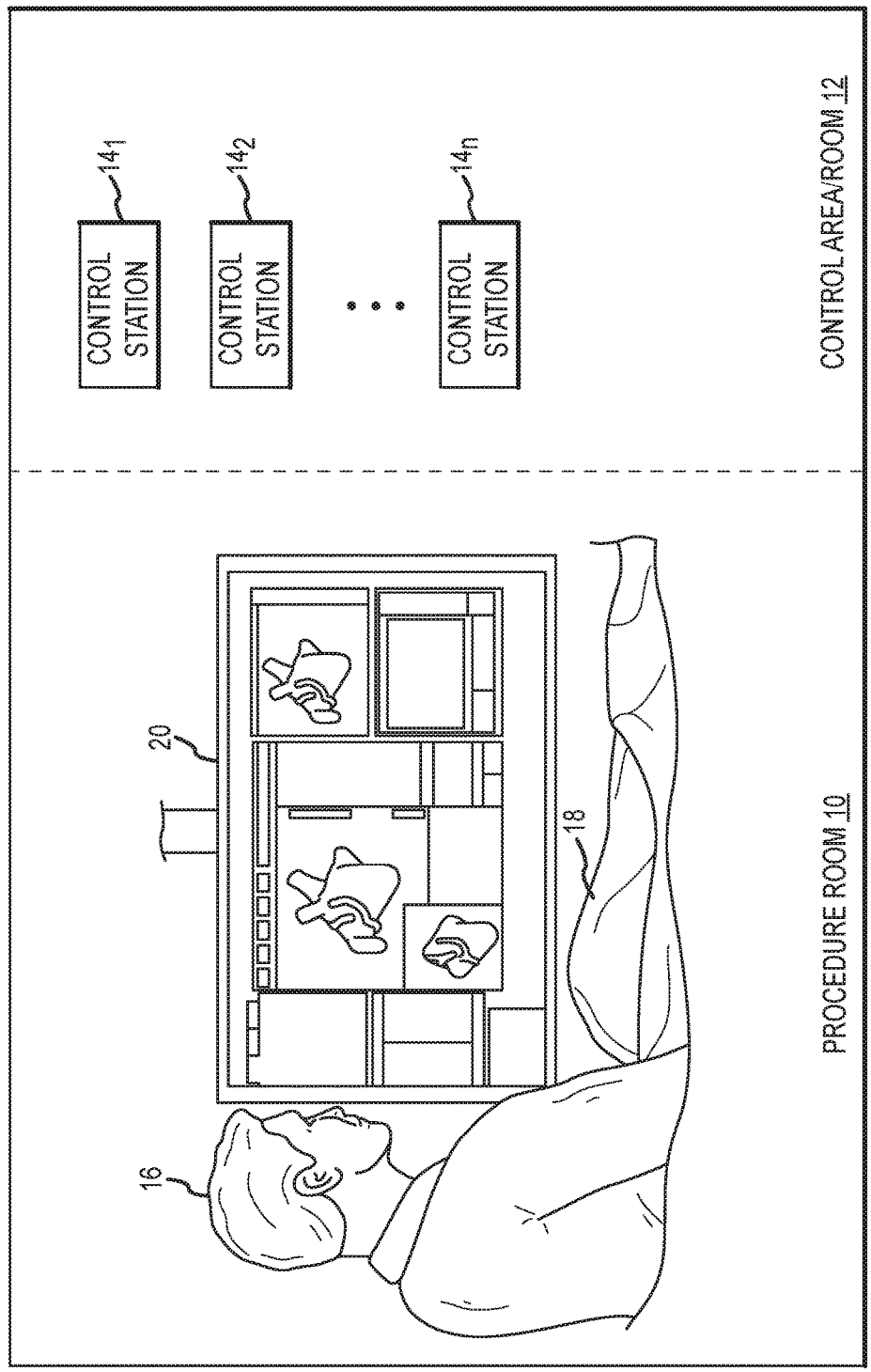
FIG. 1 is a block diagram view of a electrophysiology lab having a sterile procedure room and an associated control room.
Figure 2:
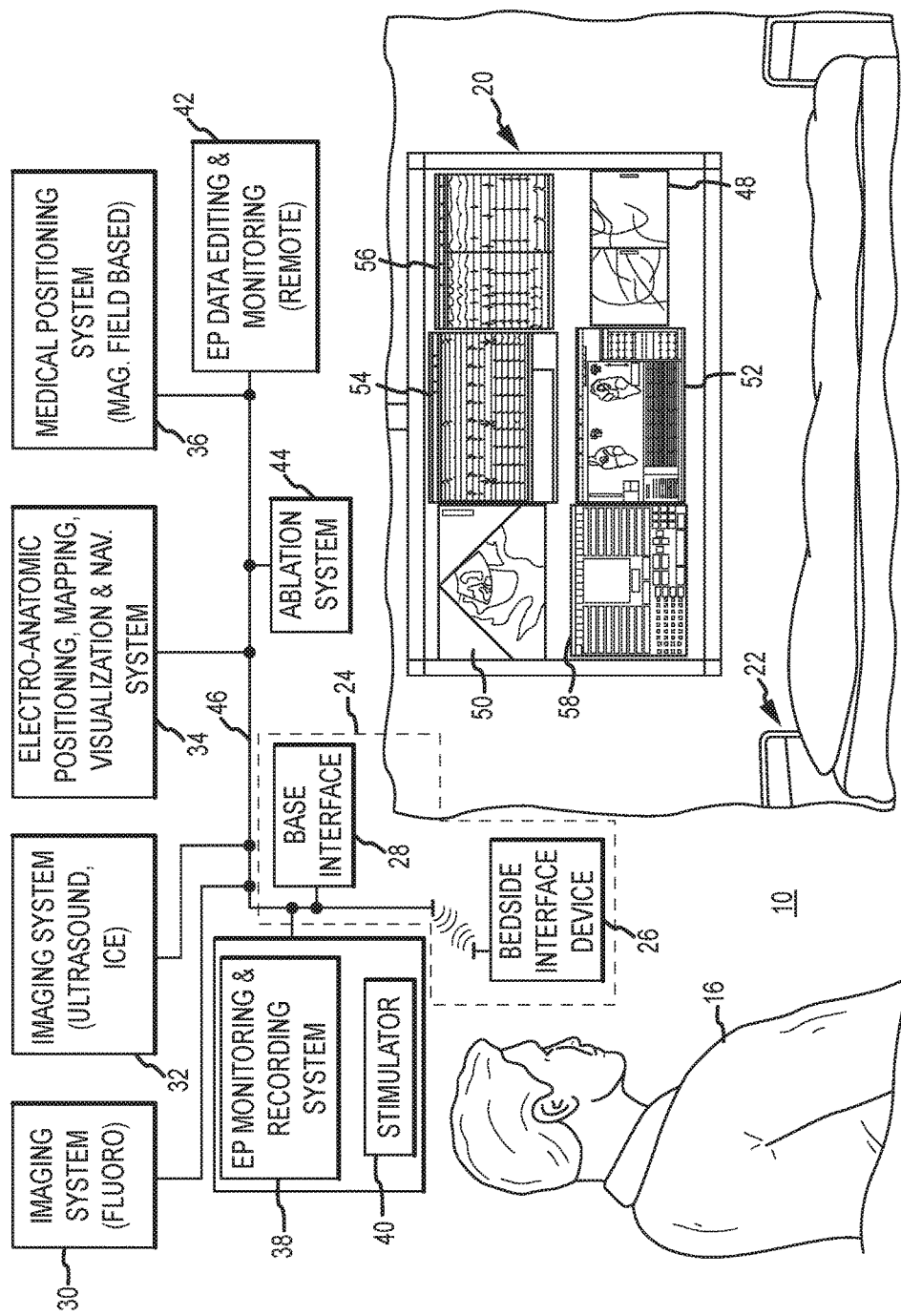
FIG. 2 is a block diagram view of an embodiment of an electrophysiology lab having a bedside interface device for controlling diagnostic and therapeutic equipment.

Referring now to the drawings wherein like reference numerals are used to identify identical or similar components in the various views, FIG. 2 is a diagrammatic overview of an electrophysiology (EP) laboratory in which embodiments of the present invention may be used. FIG. 2 shows a sterile procedure room 10 where an EP physician 16 is set to perform one or more diagnostic and/or therapeutic procedures. It should be understood that the separate control area/room 12 of FIG. 1 (not shown in FIG. 2) may continue to be used in conjunction with the bedside interface device to be described below. FIG. 2 also shows multi-display monitor 20 as well as a procedure table or bed 22. While procedure room 10 may include multiple, individual monitors, monitor 20 may be a multi-display monitor configured to display a plurality of different input channels in respective display areas on the monitor. In an embodiment, the monitor 20 may be a commercially available product sold under the trade designation VantageView™ from St. Jude Medical, Inc. of St. Paul, Minn., USA, which can have a 3840×2160 Quad-HD screen resolution with the flexibility to accept up to sixteen (16) digital or analog image inputs while displaying up to eight (8) images on one screen at one time. The procedure table 22, which may be of conventional construction, is configured to receive a patient (not shown) on whom diagnostic and/or therapeutic procedure(s) are to be performed.

FIG. 2 further shows means or apparatus 24 for facilitating physician interaction with one or more diagnostic and/or therapeutic systems. Means or apparatus 24 includes a bedside interface device 26 and optionally one or more base interfaces 28. Means or apparatus 24 provides the mechanism for the EP physician 16 to directly interact with such systems without the need for the intermediate step of verbalizing commands to a control technician, as described in connection with FIG. 1. In this regard, bedside interface device 26 is configured to present a user interface or other input logic with which the user (e.g., the EP physician 16) can directly interact or from which an input can be acquired. In multiple embodiments, various modes of interaction are presented, such as interaction via a user touch, a user multi-touch, a user gesture, a verbal command, a motion pattern of a user-controlled device, a user motion pattern and a user electroencephalogram. In addition, bedside interface device 26 can be configured to communicate with one or more of the diagnostic/therapeutic systems either wirelessly (as shown) or via a wired connection (not shown).

The base interface 28 is configured to interpret and/or facilitate directing the input acquired by the bedside interface device 26 to the appropriate one or more diagnostic and/or therapeutic systems (e.g., an electro-anatomic mapping system). In an embodiment, base interface 28 is centralized (as shown), wherein all communications with bedside device 26 occur through base interface 28. In a further embodiment, base interface 28 may be functionally distributed, wherein interface functions are located within each diagnostic or therapeutic system. In a still further embodiment, communications between bedside interface 26 and certain ones of the diagnostic/therapeutic systems can be centralized, while communications with other ones of the diagnostic/therapeutic systems can occur directly (i.e., separately).

The means or apparatus 24 addresses a number of the shortcomings of the conventional practice as described in the Background. For example, means or apparatus 24 allows the EP physician 16 to directly input levels of degree, for example, how much to rotate a view, as opposed to trying to verbally communicate "how much" to a control technician. Further, the use of means or apparatus 24 avoids the potential confusion that can sometimes occur between the EP physician and the control technician as to convention (i.e., does "rotate right" mean rotate the view or the model?). In addition, the use of means or apparatus 24 reduces or eliminates the inherent time delay between the time when the EP physician verbally issues a command and the time when the command is understood and acted upon by the technician.

With continued reference to FIG. 2, the physician 16 will typically have access to a plurality of diagnostic and/or therapeutic systems in order to perform one or more medical procedures. In the illustrative embodiment, the physician 16 may have access to a first imaging system, such as a fluoroscopic imaging system 30, a second imaging system, such as an intracardiac ultrasound or echocardiography (ICE) imaging system 32, an electro-anatomic positioning, mapping, and visualization system 34, a further positioning system, such as a medical positioning system (magnetic-field based) 36, a patient data (electrophysiological (EP) data) monitoring and recording system 38, a cardiac stimulator 40, an EP data editing/monitoring system 42 and an ablation system 44. FIG. 2 schematically shows a communication mechanism 46 which facilitates communication between and among the various systems described above. It should be understood, however, that the communications mechanism 46 may not necessarily function to enable communications between each and every system shown.

The fluoroscopic imaging system 30 may comprise conventional apparatus known in the art, for example, single plane or bi-plane configurations. A display area 48 that is shown on monitor 20 corresponds to the display output of fluoroscopic imaging system 30.

The intracardiac ultrasound and/or intracardiac echocardiography (ICE) imaging system 32 may also comprise conventional apparatus known in the art. For example, in one embodiment, the system 32 may comprise a commercial system available under the trade designation ViewMate™ Z intracardiac ultrasound system compatible with a ViewFlex™ PLUS intracardiac echocardiography (ICE) catheter, from St. Jude Medical, Inc. of St. Paul, Minn., USA. The system 32 is configured to provide real-time image guidance and visualization, for example, of the cardiac anatomy. Such high fidelity images can be used to help direct diagnosis or therapy during complex electrophysiology procedures. A display area 50 that is shown on monitor 20 corresponds to the display output of the ultrasound imaging system 32.

The system 34 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an EnSite™ Velocity™ cardiac electro-anatomic mapping system running a version of EnSite™ NavX™ navigation and visualization technology software commercially available from St. Jude Medical, Inc., of St. Paul, Minn. and as also seen generally by reference to U.S. Pat. No. 7,263,397 (the '397 patent), or U.S. Pat. No. 7,885,707 (the '707 patent). The '397 patent and the '707 patent are both hereby incorporated by reference as though fully set forth herein. System 34 can be configured to perform further advanced functions, such as motion compensation and adjustment functions. Motion compensation may include, for example, compensation for respiration-induced patient body movement, as described in U.S. application Ser. No. 12/980,515, filed 29 Dec. 2010, which is hereby incorporated by reference as though fully set forth herein. System 34 can be used in connection with or for various medical procedures, for example, EP studies or cardiac ablation procedures.

System 34 is further configured to generate and display three dimensional (3D) cardiac chamber geometries or models, display activation timing and voltage data to identify arrhythmias, and to generally facilitate guidance of catheter movement in the body of the patient. For example, a display area 52 that is shown on monitor 20 corresponds to the display output of system 34, can be viewed by physician 16 during a procedure, which can visually communicate information of interest or need to the physician. The display area 52 in FIG. 2 shows a 3D cardiac model, which, as will be described below in greater detail, may be modified (i.e., rotated, zoomed, etc.) pursuant to commands given directly by physician 16 via the bedside interface device 26.

System 36 is configured to provide positioning information with respect to suitably configured medical devices (i.e., those including a positioning sensor). System 36 may use, at least in part, a magnetic field based localization technology, comprising conventional apparatus known in the art, for example, as seen by reference to U.S. Pat. No. 7,386,339 (the '339 patent), U.S. Pat. No. 6,233,476 (the '476 patent), and U.S. Pat. No. 7,197,354 (the '354 patent). The '339 patent, the '476 patent, and the '354 patent are all hereby incorporated by reference as though fully set forth herein. System 36 may comprise MediGuide™ Technology, a medical positioning system commercially offered by MediGuide Ltd. of Haifa, Israel and now owned by St. Jude Medical, Inc. of St. Paul, Minn., USA. System 36 may alternatively comprise variants, which employ magnetic field generator operation, at least in part, such as a combination magnetic field and current field-based system such as the CARTO™ 3 System available from Biosense Webster, and as generally shown with reference to one or more of U.S. Pat. Nos. 6,498,944, 6,788,967 and 6,690,963, the entire disclosures of each of the foregoing being incorporated herein by reference as though fully set forth herein.

EP monitoring and recording system 38 is configured to receive, digitize, display and store electrocardiograms, invasive blood pressure waveforms, marker channels, and ablation data. System 38 may comprise conventional apparatus known in the art. In one embodiment, system 38 may comprise a commercially available product sold under the trade designation EP-WorkMate™ from St. Jude Medical, Inc. of St. Paul, Minn., USA. The system 38 can be configured to record a large number of intracardiac channels, may be further configured with an integrated cardiac stimulator (shown in FIG. 2 as stimulator 40), as well as offering storage and retrieval capabilities of an extensive database of patient information. Display areas 54, 56 shown on monitor 20 correspond to the display output of EP monitoring and recording system 38.

Cardiac stimulator 40 is configured to provide electrical stimulation of the heart during EP studies. Stimulator 40 can be provided in either a stand-alone configuration, or can be integrated with EP monitoring and recording system 38, as shown in FIG. 2. Stimulator 40 is configured to allow the user to initiate or terminate tachy-arrhythmias manually or automatically using preprogrammed modes of operation. Stimulator 40 may comprise conventional apparatus known in the art. In an embodiment, stimulator 40 can comprise a commercially available cardiac stimulator sold under the trade designation EP-4™ available from St. Jude Medical, Inc. of St. Paul, Minn., USA. The display area 58 shown on monitor 20 corresponds to the display output of the cardiac stimulator 40.

EP data editing/monitoring system 42 is configured to allow editing and monitoring of patient data (EP data), as well as charting, analysis, and other functions. System 42 can be configured for connection to EP data recording system 38 for real-time patient charting, physiological monitoring, and data analysis during EP studies/procedures. System 42 may comprise conventional apparatus known in the art. In an embodiment, system 42 may comprise a commercially available product sold under the trade designation EP-NurseMate™ available from St. Jude Medical, Inc. of St. Paul, Minn., USA.

To the extent the medical procedure involves tissue ablation (e.g., cardiac tissue ablation), ablation system 44 can be provided. The ablation system 44 may be configured with various types of ablation energy sources that can be used in or by a catheter, such as radio-frequency (RF), ultrasound (e.g. acoustic/ultrasound or HIFU), laser, microwave, cryogenic, chemical, photo-chemical or other energy used (or combinations and/or hybrids thereof) for performing ablative procedures. RF ablation embodiments may and typically will include other structure(s) not shown in FIG. 2, such as one or more body surface electrodes (skin patches) for application onto the body of a patient (e.g., an RF dispersive indifferent electrode/patch), an irrigation fluid source (gravity feed or pump), and an RF ablation generator (e.g., such as a commercially available unit sold under the model number IBI-1500T RF Cardiac Ablation Generator, available from St. Jude Medical, Inc.).

Figure 3A:
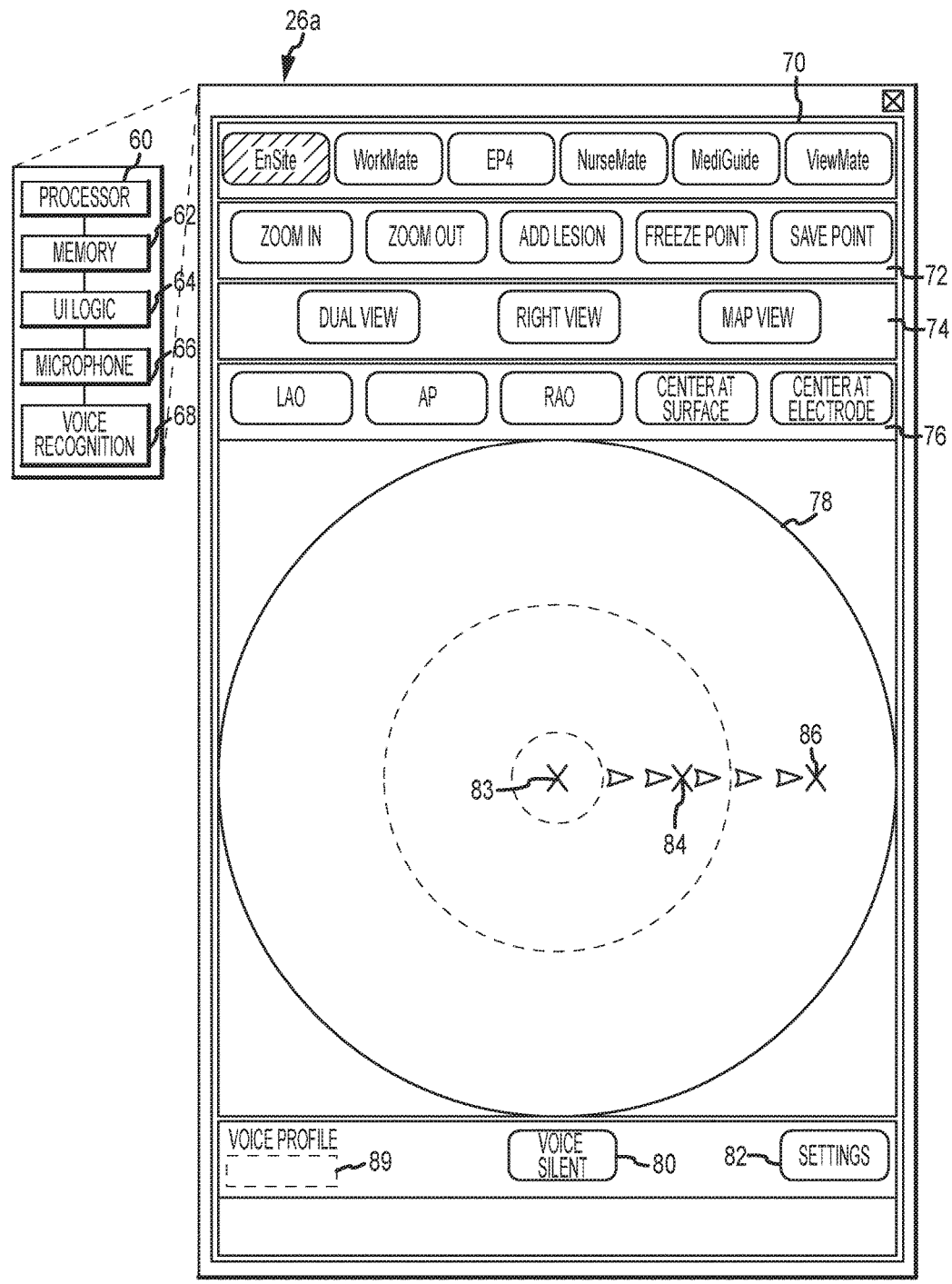
FIG. 3A is a plan view of a first embodiment of a bedside interface device comprising a touch panel computer, suitable for use in the EP lab of FIG. 2, and showing a first application-specific user interface.

FIG. 3A is a plan view of a first embodiment of a bedside interface device comprising a computer 26a, suitable for use in the EP lab of FIG. 2, and showing a first application-specific user interface. The computer 26a includes a touch-responsive display panel and thus may be referred to hereinafter sometimes as a touch panel computer. The touch panel computer 26a, as shown in inset in FIG. 3A, includes an electronic control unit (ECU) having a processor 60 and a computer-readable memory 62, user interface (UI) logic 64 stored in the memory 62 and configured to be executed by processor 60, a microphone 66 and voice recognition logic 68. In an embodiment, voice recognition logic 68 is also stored in memory 62 and is configured to be executed by processor 60. In an embodiment, the touch panel computer 26a is configured for wireless communication to base interface 28 (best shown in FIG. 2). In addition, the touch panel computer 26a is configured to draw operating power at least from a battery-based power source—eliminating the need for a power cable. The resulting portability (i.e., no cables needed for either communications or power) allows touch panel computer 26a to be carried around by the EP physician 16 or other lab staff to provide control over the linked systems (described below) while moving throughout the procedure room 10 or even the control room 12. In another embodiment, touch panel computer 26a can be wired for one or both of communications and power, and can also be fixed to the bedrail or in the sterile field.

In the illustrated embodiment, the UI logic 64 is configured to present a plurality of application-specific user interfaces, each configured to allow a user (e.g., the EP physician 16) to interact with a respective one of a plurality of diagnostic and/or therapeutic systems (and their unique interface or control applications). As shown in FIG. 3A, the UI logic 64 is configured to present on the touch panel surface of computer 26a a plurality of touch-sensitive objects (i.e., "buttons", "flattened joystick", etc.), to be described below. In the illustrative embodiment, the UI logic 64 produces a first, application-selection group of buttons, designated as group 70, and which are located near the top of the touch panel. Each of the buttons in group 70 are associated with a respective diagnostic and/or therapeutic system (and control or interface application therefore). For example, the six buttons labeled "EnSite", "WorkMate", "EP4", "NurseMate", "MediGuide", "ViewMate" correspond to electro-anatomic mapping system 34 (for mapping control), EP recording system 38 (for patient data recording control), stimulator 40 (for stimulator control), EP data editing and monitoring system 42 (for charting) and ultrasound imaging system 32 (for ultrasound control), respectively.

When a user selects one of the buttons in group 70, the UI logic 64 configures the screen display of computer 26a with an application-specific user interface tailored for the control of and interface with the particular EP system selected by the user. In FIG. 3A, the "EnSite" system is selected, so the UI logic 64 alters the visual appearance of the "EnSite" button so that it is visually distinguishable from the other, non-selected buttons in group 70. For example, when selected, the "EnSite" button may appear depressed or otherwise shaded differently than the other, non-selected buttons in group 70. This always lets the user know what system is selected. The UI logic 64, in an embodiment, also maintains the application-selection buttons in group 70 at the top of the screen regardless of the particular application selected by the user. This arrangement allows the user to move from system (application) to system (application) quickly and control each one independently.

With continued reference to FIG. 3A, UI logic 64 presents an application-specific user interface tailored and optimized for control of and interaction with system 34. This user interface includes a second, common-task group of selectable buttons, designated group 72, a third, view-mode group of selectable buttons, designated group 74, a fourth, view-select group of selectable buttons, designated group 76, a flattened joystick 78 configured to receive view-manipulation input from the user, a voice recognition control button 80, and a settings button 82. Each group will be addressed in turn.

The second group 72 of buttons includes a listing of common tasks performed by an EP physician when interacting with system 34. Each of the buttons in group 72 are associated with a respective task (and resulting action). For example, the five buttons in group 72 are labeled "Zoom In", "Zoom Out", "Add Lesion", "Freeze Point", and "Save Point". The "Zoom In" and "Zoom Out" buttons allow the user to adjust the apparent size of the 3D model displayed on monitor 20 (i.e., enlarging or reducing the 3D model on the monitor).

Figure 4A:
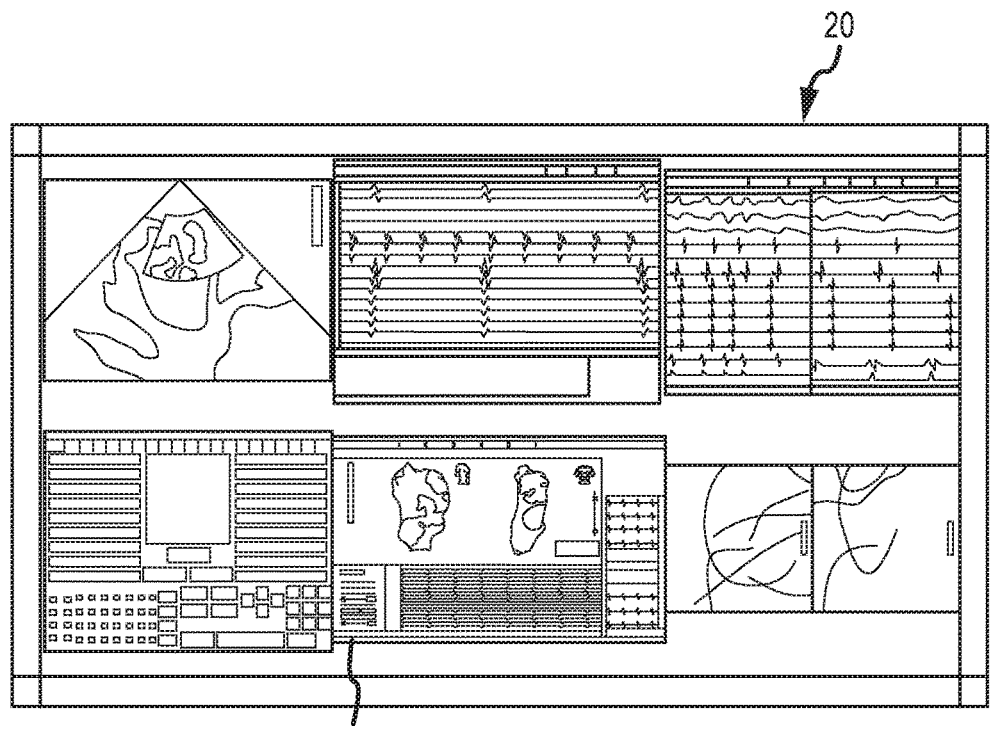
FIG. 4A is a view of a monitor shown in FIG. 2, showing multiple inset displays associated with a plurality of diagnostic and/or therapeutic systems.
Figure 4B:
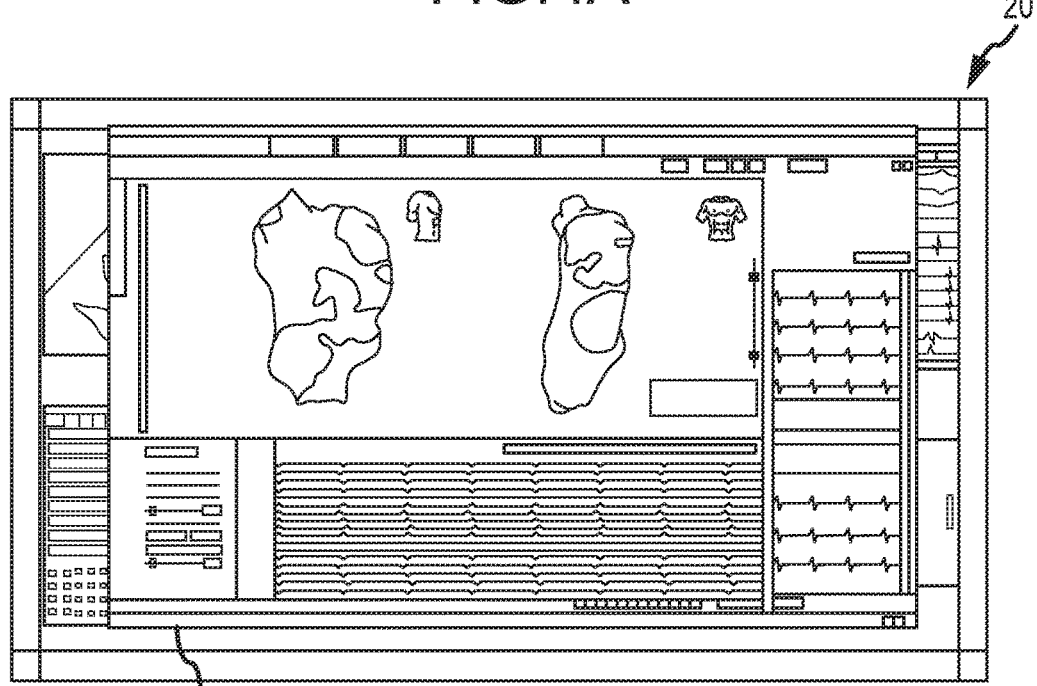
FIG. 4B is a view of the monitor of FIG. 4A, showing a zoomed-in window of the display associated with an electroanatomic mapping system.

For example, FIG. 4A is a view of the monitor 20 of FIG. 2, showing multiple inset displays for different applications, where the display area (window) $52_1$ shows the EnSite™ display output of a 3D electro-anatomic model at a first magnification level. FIG. 4B is a further view of monitor 20, showing a zoomed-in view of the same display area (window), now designated $52_2$, which has an increased magnification level and thus apparent size. This change of course allows the physician to see details in window $52_2$ that may not be easy to see in window $52_1$.

Referring again to FIG. 3A, the "Add Lesion" button is configured to add a lesion marker to the 3D model. Other commands can be also be executed using the "Freeze Point" and "Save Point" buttons. It should be understood that variations are possible.

Each of the buttons in group 74 are associated with a respective display mode, which alters the display output of system 34 to suit the wishes of the physician. For example, the three selectable buttons labeled "Dual View", "Right View", and "Map View" re-configure the display output of system 34, as will appear on monitor 20.

Each of the buttons in group 76 are associated with a respective viewpoint from which the 3D electro-anatomic model is "viewed" (i.e., as shown in window 52 on monitor 20). Three of the five selectable buttons, namely those labeled "LAO", "AP", and "RAO", allow the user to reconfigure the view point from which the 3D electro-anatomic model is viewed (i.e., left anterior oblique, anterior-posterior, right anterior oblique, respectively). The remaining two buttons, namely those labeled "Center at Surface" and "Center at Electrode" allow the user to invoke, respectively, the following functions: (1) center the anatomy shape in the middle of the viewing area; and (2) center the current mapping electrode or electrodes in the middle of the viewing area.

The flattened joystick 78 is a screen object that allows the user to rotate the 3D model displayed in the window 52. In addition, as the point of contact (i.e., physician's finger) with the joystick object 78 moves from the center or neutral position, for example at point 83, towards the outer perimeter (e.g., through point 84 to point 86), the magnitude of the input action increases. For example, the acceleration of rotation of the model or cursor will increase. While FIG. 3A shows the joystick object 78 as having three (3) gradations or concentric bands, it should be appreciated that this is for clarity only and not limiting in number. For example, in an embodiment, a relatively larger number of gradations or bands, such as ten (10), may be provided so as to effectively provide for a substantially continuous increase in sensitivity (or magnitude) as the point of contact moves toward the outer radius. In another embodiment, a single gradient may be continuous from the center position, point 83, to the outer edge of the joystick object 78, with the centermost portion of the gradient being the brightest in intensity or color and the outermost portion of the gradient being the darkest in intensity or color, for example. In yet another embodiment, a single gradient may be continuous from the center position, point 83, to the outer edge of the joystick object 78, with the centermost portion of the gradient being the darkest in intensity or color and the outermost portion of the gradient being brightest in intensity or color, for example.

In a further embodiment, UI logic 64 can be further configured to present an additional button labeled "Follow Me" (not shown), which, when selected by the user, configures the electro-anatomic mapping system 34 for "follow me" control. This style of control is not currently available using a conventional keyboard and mouse interface. For "follow me" control, UI logic 64 is configured to receive a rotation input from the user via the touch panel (e.g., joystick 78); however, the received input is interpreted by system 34 as a request to rotate the endocardial surface rendering (the "map") while maintaining the mapping catheter still or stationary on the display. In an embodiment, the physician can set the position and orientation of the mapping catheter, where it will remain stationary after the "Follow Me" button is selected.

Another feature of the touch panel computer 26a is that it incorporates, in an embodiment, voice recognition technology. As described above, computer 26a includes microphone 66 for capturing speech (audio) and voice recognition logic 68 for analyzing the captured speech to extract or identify spoken commands. The voice recognition feature can be used in combination with the touch panel functionality of computer 26a. The microphone 66 may comprise conventional apparatus known in the art, and can be a voice recognition optimized microphone particularly adapted for use in speech recognition applications (e.g., an echo cancelling microphone). Voice recognition logic 68 may comprise conventional apparatus known in the art. In an embodiment, voice recognition logic 68 may be a commercially available component, such as software available under the trade designation DRAGON DICTATION™ speech recognition software.

In an embodiment, computer 26a is configured to recognize a defined set of words or phrases adapted to control various functions of the multiple applications that are accessible or controllable by computer 26a. The voice recognition feature can itself be configured to recognize unique words or phrases to selectively enable or disable the voice recognition feature. Alternatively (or in addition to), a button, such as button 80 in FIG. 3A, can be used to enable or disable the voice recognition feature. In this regard, the enable/disable button can be either a touch-sensitive button (i.e., screen object), or can be hardware button.

Voice recognition logic 68 is configured to interact with the physician or other user to "train" the logic (e.g., having the user speak known words) so as to improve word and/or phrase recognition. The particulars for each user so trained can be stored in a respective voice (user) profile, stored in memory 62. For example, in FIG. 3A, the currently active voice profile is listed in dashed-line box 89. In an embodiment, each user can have unique commands, which may also be stored in the respective voice profile. In a further embodiment, the language need not be English, and can be other languages. This flexibility as to language choice enlarges the audience of users who can use the device 26a. The voice recognition feature presents a number of advantages, including the fact that the physician 16 does not have to remove his/her hands from the catheter or other medical device being manipulated. In addition, the absence of contact or need to touch computer 26a maintains a sterile condition. The voice recognition feature can also be used either alone or in combination with other technologies.

With continued reference to FIG. 3A, UI logic 64 also presents a "Settings" button 82. When the "Settings" button 82 is selected, UI logic 64 generates another screen display that allows the user to adjust and/or set/reset various settings associated with the application currently selected. In an embodiment, the "Settings" button can also allow adjustment of parameters that are more global in nature (i.e., apply to more than one application). For example only, through "Settings", the physician or another user can edit all of the phrases associated with a particular physician or specify a timeout (i.e., the elapsed amount of time, after which the computer will stop listening (or not) for voice commands). The physician or another user can also edit miscellaneous parameters, such as communication settings and the like.

Figure 3B:
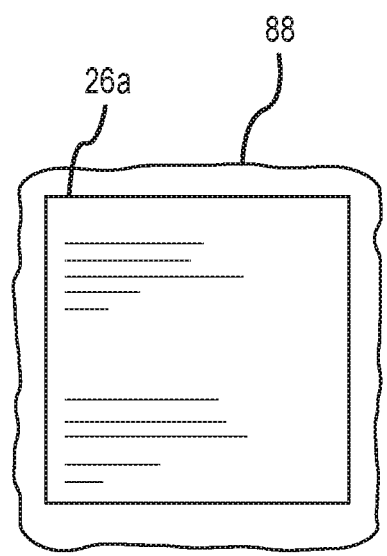
FIG. 3B is an isometric view of a sterile drape configured to isolate the touch panel computer of FIG. 3A.

FIG. 3B is an isometric view of a sterile drape 88 configured to protect the touch panel computer 26a of FIG. 3A from contamination and to maintain the physician's sterility. Conventional materials and construction techniques can be used to make drape 88.

Figure 5:
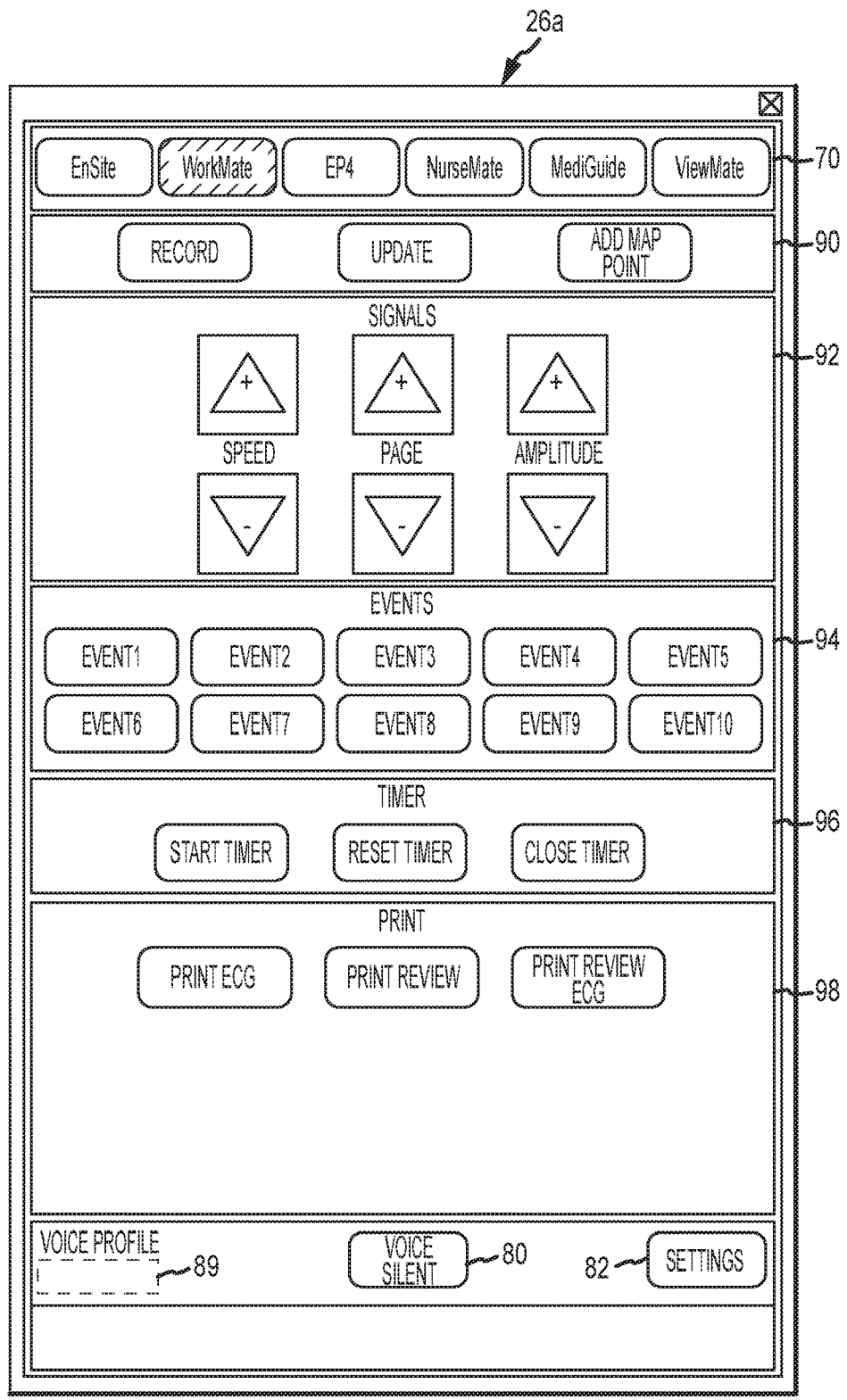
FIG. 5 is a plan view of the touch panel computer of FIG. 3A showing a second application-specific user interface.

FIG. 5 is a plan view of touch panel computer 26a showing a different application-specific user interface, now relating to EP monitoring and recording system 38 (i.e., "EP-WorkMate"). In the illustrative embodiment, UI logic 64 produces the same application-selection group 70 of buttons along the top of the touch panel, for quick and easy movement by the user between applications. A second, common-tasks group of buttons, designated as group 90, are shown below group 70. For example, the three buttons labeled "Record", "Update", and "Add Map Point" can execute the identified function. Likewise, additional groups of buttons are shown, grouped by function, for example the signals-adjustment group 92, the events group 94, the timer group 96 and the print group 98. It should be understood that variations are possible, depending on the items that can be adjusted or controlled on the destination system. It warrants emphasizing that UI logic 64 thus presents a unique user interface tailored to the requirements of the particular application selected. Each group includes items that are commonly asked for by the physician. For example, in the signals group 92, the Speed +/− buttons can be used to change the viewed waveform sweep speed as the physician may need more or less detail; the Page +/− buttons can be used to change the page of signals being viewed (e.g., from surface ECG signals to intracardiac signals); and the Amplitude +/− buttons can be used to change the signal amplitudes up or down. As a further example, in the Events group 94, the enumerated Events buttons cause a mark to be created in the patient charting log to indicate a noteworthy (i.e., important) item or event, such as the patient was just defibrillated or entered a tachy-arrhythmia. Note that these items are all user definable and speakable (capable of being tied to the voice recognition function). The physician also needs to keep track of certain periods of time. Thus, in the Timer group 96, the timer buttons can be used to keep track of such periods of time, for example, such as a certain time after an ablation (e.g., 30 minutes) to verify that the ablation procedure is still effective. Finally, regarding the print group 98, various print buttons are provided so as to avoid requiring a physician to verbally indicate (e.g., by way of shouting out "print that document to the case" or the like) and to include such documents in a final report.

Figure 6:
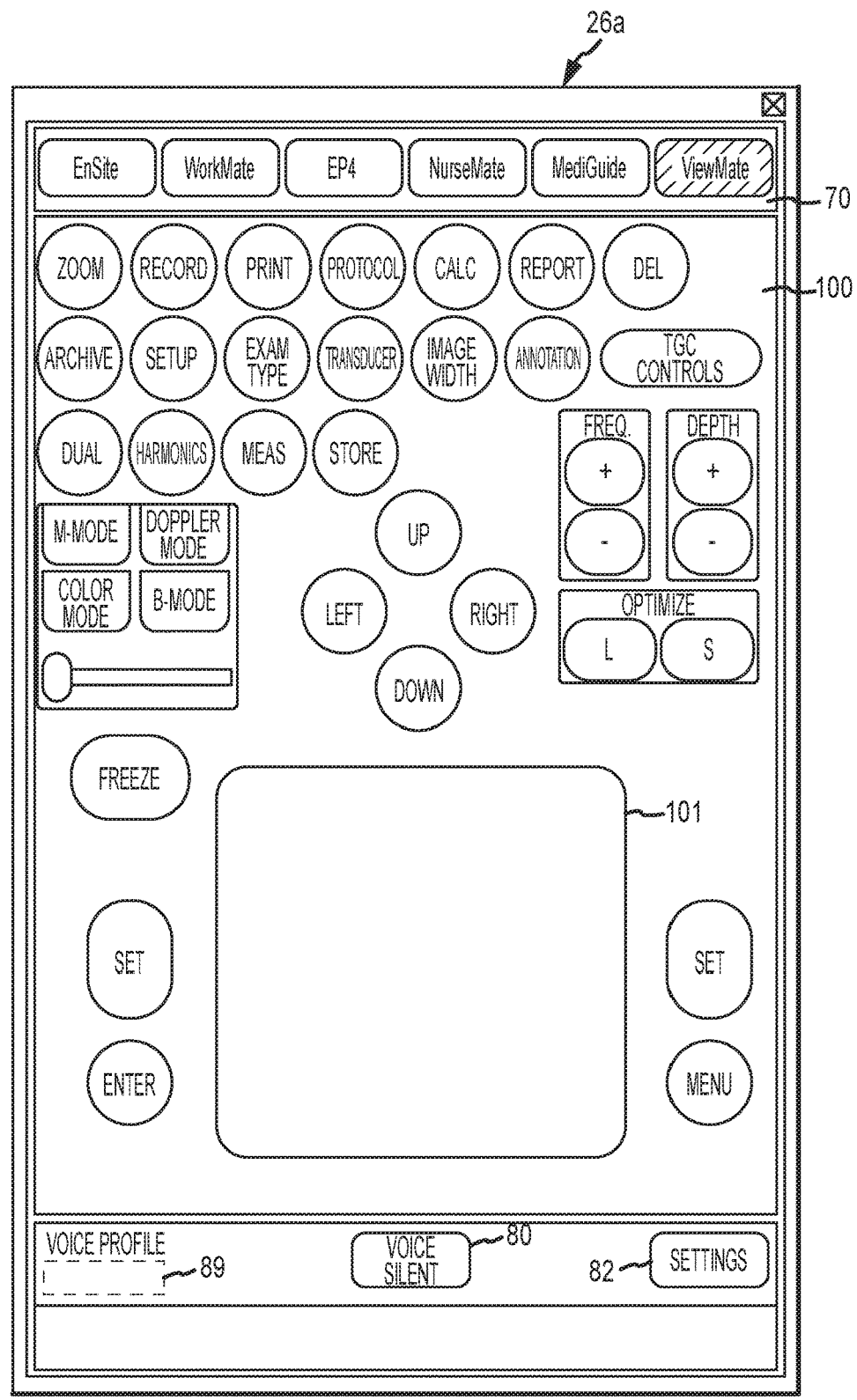
FIG. 6 is a plan view of the touch panel computer of FIG. 3A showing a third application-specific user interface.

FIG. 6 is a plan view of touch panel computer 26a showing in exemplary fashion a further, different application-specific user interface relating to the ultrasound imaging system 32 ("ViewMate"). As with the other application-specific user interfaces, the user interface presented in FIG. 6 repeats the common, application-selection group of buttons, designated group 70. A further group of buttons and adjustment mechanisms are located in group 100. The controls (buttons, sliders) provided for this user interface completely eliminate the need to have a separate ultrasound keyboard to control the console. The user interface shown can be different, independent on the kind of machine being controlled, but at a minimum may typically provide a way to control the receive gain, the depth setting, the focus zone, the TGC (i.e., time gain compensation) curve, the monitoring mode (e.g., B, M, color Doppler, Doppler), image recording, as well as other image attributes and states. Note, trackpad object 101 is shown in the center of the user interface. The capability provided by UI logic 64 to rapidly switch applications and present to the bedside user an application-specific user interface minimizes or eliminates many of the shortcomings set forth in the Background.

It should be understood that variations in UI logic 64 are possible. For example, certain applications can be linked (in software) so that multiple applications can be controlled with a single command (e.g., the Record command). In another embodiment, UI logic 64 can be configured to provide additional and/or substitute functions, such as, without limitation, (1) map creation; (2) collecting points; (3) segmenting regions by anatomy; (4) map view (rotate and zoom); (5) select/manipulate a number of maps and view each; (6) selection of signal trace display; (7) adjust EP signal amplitude; (8) sweep speed; (9) provide single button (or touch, multi-touch, gesture) for recording a segment, placing an event marker, and/or placing a lesion marker.

It should be further understood that the screen layouts in the illustrative embodiment are exemplary only and not limiting in nature. The UI logic 64 can thus implement alternative screen layouts for interaction by the user. For example, while the screen displays in FIGS. 3A, 5 and 6 show an approach that incorporates the top level menu items on every screen, multi-level menus can also be used. For example, the screen layouts can be arranged such that a user descends down a series of screens to further levels of control. To return to upper levels (and to the "home" screen), a "Back" button or the like can be provided. Alternatively, a "Home" button can be provided.

In a still further embodiment, UI logic 64 can be configured for bi-directional display of information, for example, on the touch-responsive display panel. As one example, the "EnSite" user interface (FIG. 3A) can be configured so that the EnSite™ model is sent to the computer 26a and displayed on the touch-responsive display panel. The user interface provided by UI logic 64 can allow the user to drag his or her finger on the panel to rotate the model. The display of the model provides context with respect to the act of dragging. Other information can be displayed as well, such as a waveform. In various embodiments, all or a portion of the items/windows displayed on monitor 20 (see, e.g., FIGS. 2, 4A, and 4B) may be displayed or mirrored on the touch-responsive display panel. For example, display area or window 52 may be displayed on the touch-responsive display panel allowing the physician or other user to directly modify the features of window 52 at the patient's bedside. Other display areas/windows, such as windows 50, 54, 56, 58, and/or 48 (see FIG. 2) may also be displayed and/or modified on the touch-panel display panel. One further example involves displaying feedback information or messages originating from the various devices or systems back to the touch-responsive display panel. In this regard, the UI logic 64 can configure any of the user-interfaces to have a message area, which can show informational messages, warning messages or critical error messages for viewing by the user. The message area feature provides a way to immediately alert the physician to such messages, rather than the physician having to watch for messages on multiple displays.

Figure 7A:
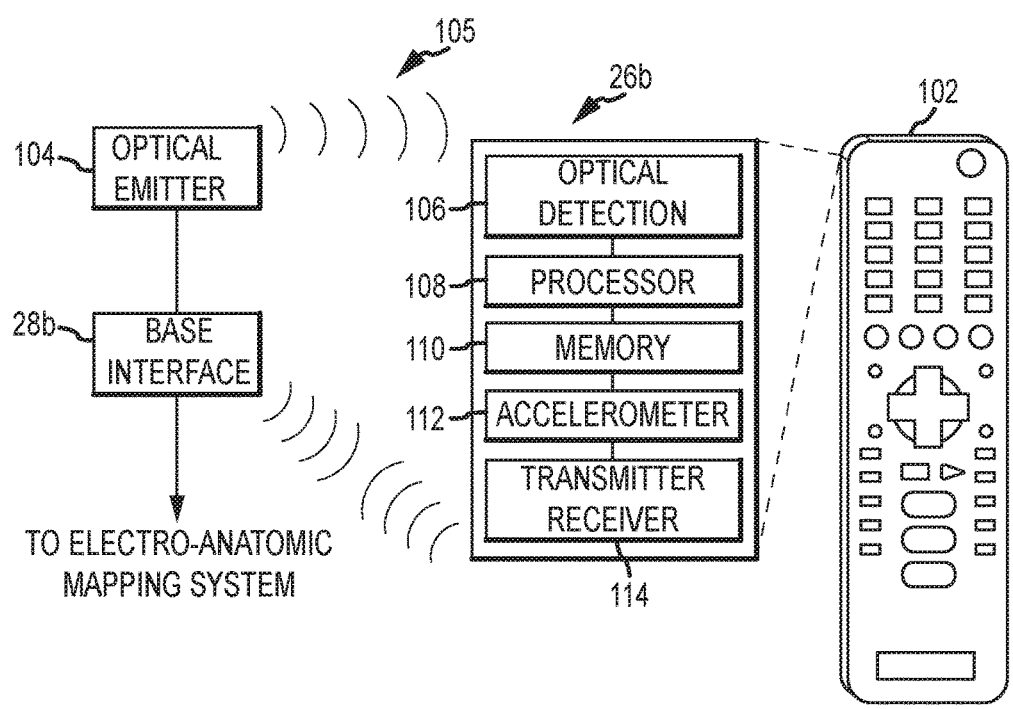
FIG. 7A is a diagrammatic and block diagram view of a second embodiment of the bedside interface device comprising an electronic wand system.

FIG. 7A is a diagrammatic and block diagram view of a second embodiment of the bedside interface device, comprising an electronic wand system 26b. As with touch panel computer 26a, wand system 26b is configured to allow the EP physician to take control, bedside of the patient, of an EP diagnostic or therapeutic system, such as the electro-anatomic mapping system 34. The wand system 26b includes a wireless remote control portion 102, an optical emitter portion 104, and a base interface 28b, which may be coupled to the desired, target EP system through either a wired or wireless connection. The wand system 26b incorporates remote control technology, and includes the ability to detect and interpret motion of the remote control indicative of an EP physician's command or other instruction, detect and interpret key-presses on the remote control, and/or detect and interpret motion/keypress combinations.

Since the wand system 26b is contemplated as being used in the sterile procedure room, multiple embodiments are contemplated for avoiding contamination. In this regard, wand system 26b may be configured with a disposable remote control portion 102, with a reusable remote control portion 102 that is contained within an enclosure compatible with sterilization procedures, with a reusable remote control portion 102 adapted to be secured in a sterilization-compatible wrapper, or with a reusable remote control portion 102 that is encased in a sterile but disposable wrapper.

With continued reference to FIG. 7A, remote control portion 102 may include an optical detector 106, an electronic processor 108, a memory 110, an optional accelerometer 112 and a wireless transmitter/receiver 114. The processor 108 is configured to execute a control program that is stored in memory 110, to achieve the functions described below. The optical emitter 104 is configured to emit a light pattern 105 that can be detected and recognized by optical detector 106. For example, the light pattern may be a pair of light sources spaced apart by a predetermined, known distance. The control program in remote 102 can be configured to assess movement of the light pattern 105 as detected by detector 106 (e.g., by assessing a time-based sequence of images captured by detector 106). For example, in the exemplary light pattern described above, processor 108 can be configured to determine the locations of the light sources (in pixel space). In an embodiment, the control program in remote 102 may only discern the light pattern 105 itself (e.g., the locations in pixel space) and transmit this information to base interface 28b, which in turn assesses the movement of the detected light pattern in order to arrive at a description of the motion of the remote 102. In a still further embodiment, various aspects of the processing may be divided between processor 108 and a processor (not shown) contained in base interface 28b. The processor 106 communicates with base interface 28b via the wireless transmitter/receiver 114, which may be any type of wireless communication method now known or hereafter developed (e.g., such as those technologies or standards branded Bluetooth™, Wi-Fi™, etc.). The processor 108 is configured to transmit wirelessly to interface 28b the detected keypresses and information concerning the motion of the remote control 102 (e.g., the information about or derived from the images from the optical detector 106). In an embodiment, the motion of remote control 102 may also be determined, or supplemented by, readings from accelerometer 112 (which may be single-axis or multi-axis, such as a 3-axis accelerometer). In some instances, rapid motion may be better detected using an accelerometer than using optical methods. In an embodiment, electronic wand system 26b may be similar to (but differing in application, as described herein) a commercially available game controller sold under the trade designation Wii Remote Controller, from Nintendo of America, Inc.

Either the remote 102 or the base interface 28b (or both, potentially in some division of computing labor) is configured to identify a command applicable to the one of the EP diagnostic/therapeutic systems, such as electro-anatomic mapping system 34, based on the detected motion of the remote 102. Alternatively, the command may be identified based on a key press, or a predetermined motion/key press combination. Once the remote 102 and/or interface 28b identifies the command it is transmitted to the appropriate EP system. In an electro-anatomic mapping system embodiment, the wireless remote control 102 is configured to allow an EP physician to issues a wide variety of commands, for example only, any of the commands (e.g., 3D model rotation, manipulation, etc.) described above in connection with touch panel computer 26a. By encoding at least some of the control through the wireless remote control 102 that the EP physician controls, one or more of the shortcomings of conventional EP labs, as described in the Background, can be minimized or eliminated. As with touch panel computer 26a, electronic wand system 26b can reduce procedure times as the EP physician will spend less time playing "hot or cold" with the mapping system operator (i.e., the control technician), but instead can set the display to his/her needs throughout the medical procedure.

Figure 7B:
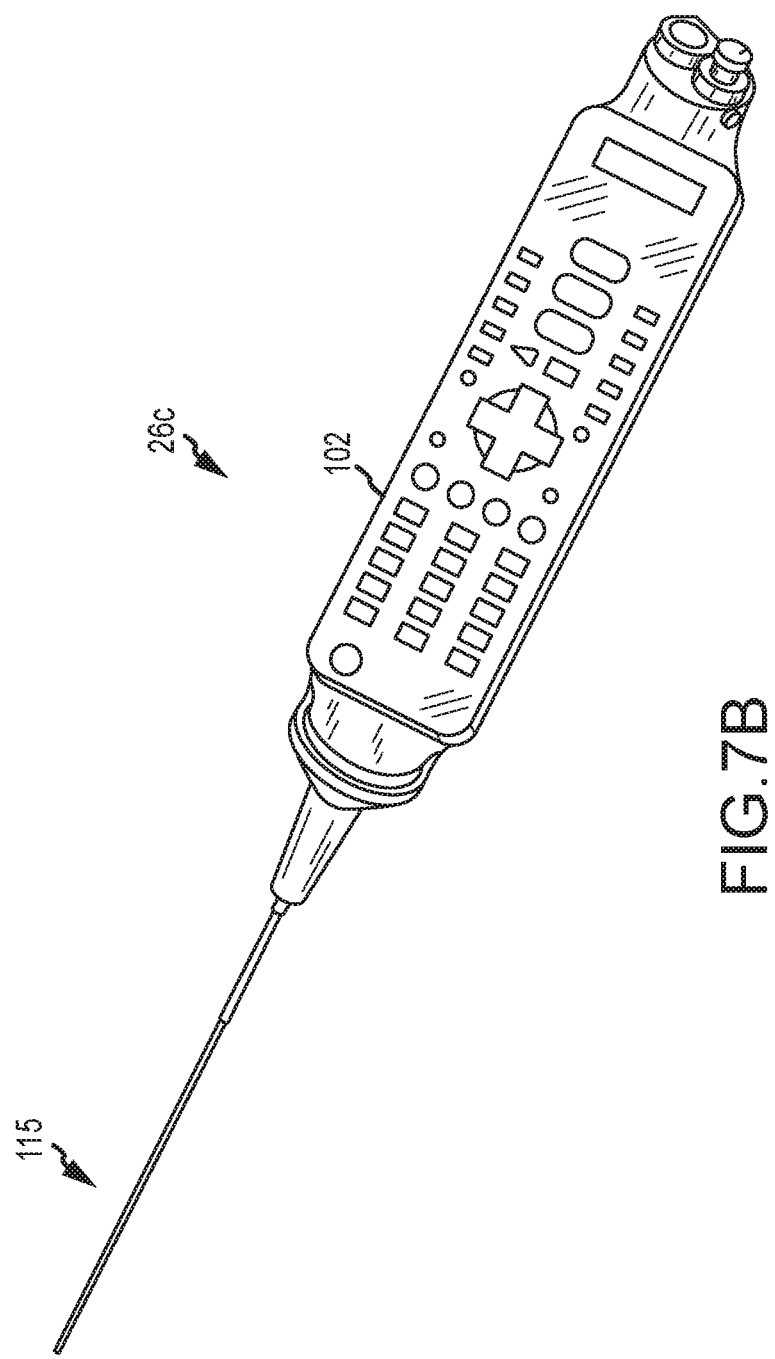
FIG. 7B is a diagrammatic view of a third embodiment of the bedside interface device wherein a catheter is integrated with the remote control portion of FIG. 7A.

FIG. 7B shows a further embodiment, designated interface device 26c. Interface device 26 integrates the remote control 102 described above into the handle of a catheter 115. Through the foregoing, the physician need not take his hands off the catheter, but rather can issue direct, physical commands (e.g., via key-presses) while retaining control of the catheter. Additionally, one or more of the keys or a slider switch on the catheter handle may serve as a safety mechanism to prevent inadvertent activation of one or more commands while operating the catheter. In such an embodiment, after advancing the catheter into a patient's body, the safety mechanism may be deactivated or otherwise turned off such that the physician can issue commands and then he or she may reactivate or turn on the safety mechanism and resume manipulating the catheter without fear of modifying the view or model shown on an on-screen display, for example. The catheter 115 may further comprise one or more electrodes on a distal portion of the catheter shaft and a manual or motorized steering mechanism (not shown) to enable the distal portion of the catheter shaft to be steered in at least one direction. In at least one embodiment, the catheter handle may be generally symmetric on opposing sides and include identical or nearly identical sets of controls on opposing sides of the handle so that a physician need not worry about which side of the catheter handle contains the keys. In another embodiment, the catheter handle may be generally cylindrical in shape and include an annular and/or rotatable control feature for issuing at least one command, again so the physician need not worry about the catheter handle's orientation in his or her hand(s). Exemplary catheters, handles, and steering mechanisms are shown and described in U.S. Pat. No. 5,861,024, U.S. application Ser. No. 12/861,555, filed 23 Aug. 2012 (the '555 application), U.S. Pat. Nos. 7,465,288, and 6,671,533, each of which is hereby incorporated by reference as though fully set forth herein.

Figure 8:
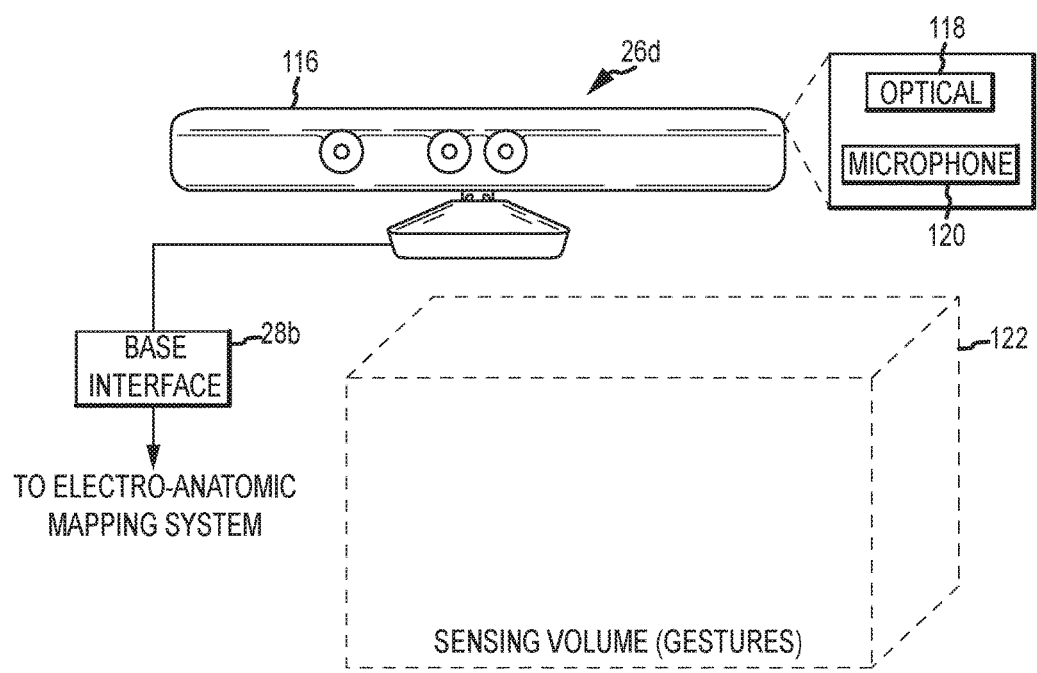
FIG. 8 is a diagrammatic and block diagram view of a fourth embodiment of the bedside interface device comprising a motion capture apparatus.

FIG. 8 is a diagrammatic and block diagram view of a fourth embodiment of the bedside interface device, comprising a motion capture apparatus 26d. As with touch panel computer 26a, wand system 26b and integrated system 26c, motion capture apparatus 26d is configured to allow the EP physician to take control, bedside of the patient, of an EP diagnostic or therapeutic system, such as electro-anatomical mapping system 34. The motion capture apparatus 26d includes a capture apparatus 116 having both an optical sub-system 118 and a microphone sub-system 120 where the apparatus 116 is coupled to a base interface 28b. The apparatus 116 is configured to optically detect the motion or physical gestures of the EP physician or other user when such movements occur within a sensing volume 122. The base interface 28b may be coupled to the desired, target EP system through either a wired or wireless connection.

The motion capture apparatus 26d includes the capability to detect hand/arm/leg/trunk/facial motions (e.g., gestures) of the EP physician or other user and translate the detected patterns into a desired command. Apparatus 26d also includes audio capture and processing capability and thus also has the capability to detect speech and translate the same into desired commands. In an embodiment, apparatus 26d is configured to detect and interpret combinations and sequences of gestures and speech into desired commands. The base interface 28b is configured to communicate the commands (e.g., rotation, zoom, pan of a 3D anatomical model) to the appropriate EP diagnostic or therapeutic system (e.g., the electro-anatomic mapping system 34). In an embodiment, the motion capture apparatus 26d may comprise commercially available components, for example, the Kinect™ game control system, available from Microsoft, Redmond, Wash., USA. A so-called Kinect™ software development kit (SDK) is available, which includes drivers, rich application programming interfaces (API's), among other things contents, that enables access to the capabilities of the Kinect™ device. In particular, the SDK allows access to raw sensor streams (e.g., depth sensor, color camera sensor, and four-element microphone array), skeletal tracking, advanced audio (i.e., integration with Windows speech recognition) as well as other features.

Since there is no contact contemplated by EP physician 16 during use of motion capture apparatus 26d, contamination and subsequent sterilization issues are eliminated or reduced. In addition, the lack of contact with apparatus 26d for control purposes allows the EP physician to keep his hands on the catheter or other medical device(s) being manipulated during an EP procedure. By encoding at least some of the control through the motion capture apparatus 26d, with which the EP physician interacts, one or more of the shortcomings of conventional EP labs, as described in the Background, can be minimized or eliminated. As with the previous embodiments, the motion capture apparatus 26d can reduce procedure times.

It should be understood that variations are possible. For example, the motion capture apparatus 26d can be used in concert with sensors and/or emitters in a sterile glove to assist the apparatus 26d to discriminate commands intended to be directed to one of the EP systems, versus EP physician hand movements that result from his/her manipulation of the catheter or medical device, versus other movement in the EP lab in general. In another embodiment, the motion capture apparatus 26d may discriminate such commands by being "activated" by a user when a specific verbal command is issued (e.g., "motion capture on") and then "deactivated" by the user when another specific verbal command is issued (e.g., "motion capture off").

Figure 9:
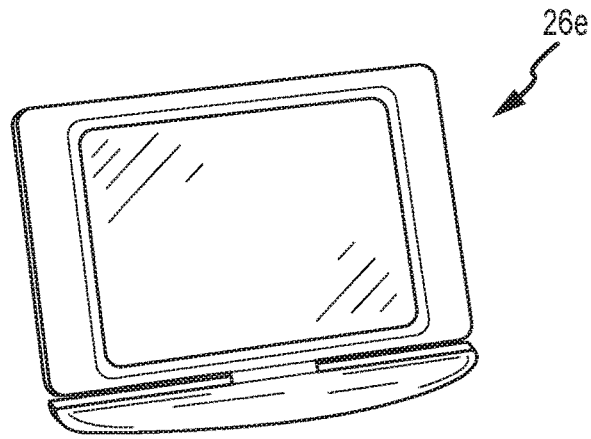
FIGS. 9-10 are diagrammatic views of fifth and sixth embodiments of the bedside interface device comprising touch responsive surface devices that can be covered in a sterile bag.
Figure 10:
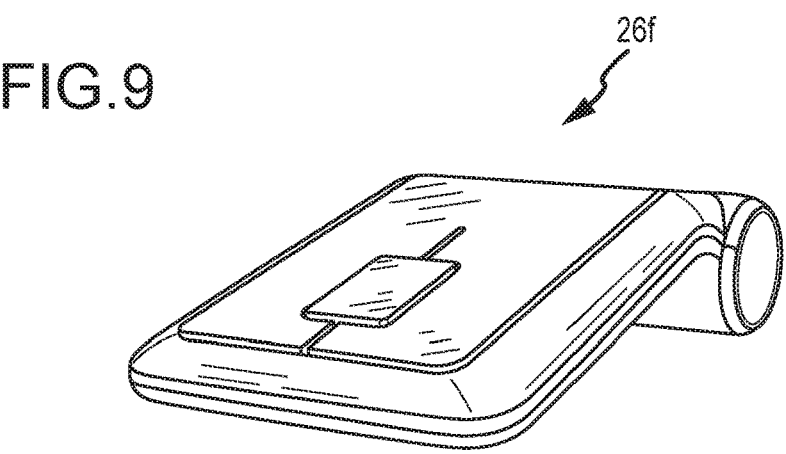

FIGS. 9-10 are diagrammatic views of fifth and sixth embodiments of the bedside interface device, comprising touch responsive devices. FIGS. 9 and 10 show touch-screen mouse pad devices 26e and 26f, respectively. These devices can be covered in a sterile bag. The EP physician 16 can move the mouse cursor from application to application and control each such application independently. Devices 26e, 26f may comprise conventional apparatus known in the art.

Figure 11:
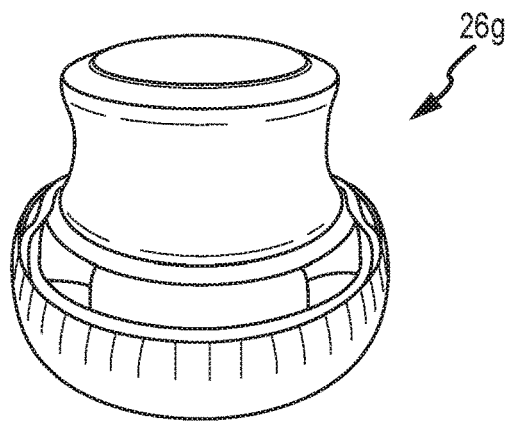
FIG. 11 is a diagrammatic view of a seventh embodiment of the bedside interface device comprising a customized joystick that can be covered in a sterile bag.

FIG. 11 is a diagrammatic view of a seventh embodiment of the bedside interface device comprising a customized joystick 26g. Joystick 26g can also be covered in a sterile bag. The device 26g can be used to be provide application-specific control a particular application function(s), such as rotating a 3D model (system 34), adding lesion markers, and the like.

Figure 12:
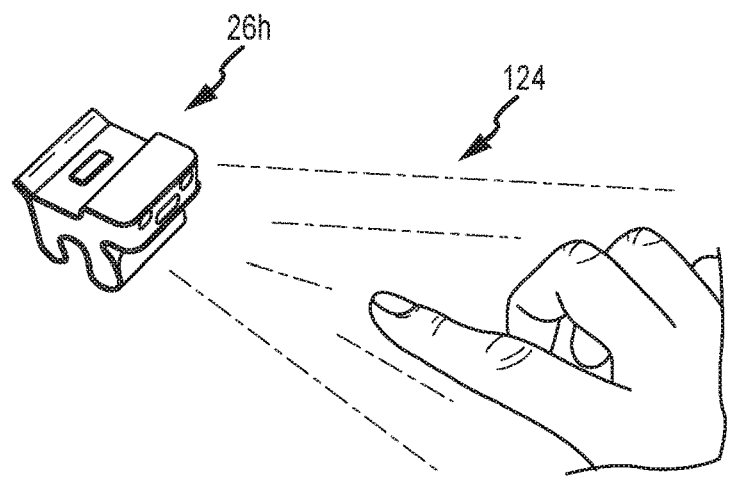
FIGS. 12-13 are diagrammatic views of eighth and ninth embodiments of the bedside interface device comprising holographic mouse and keyboard input devices, respectively.
Figure 13:
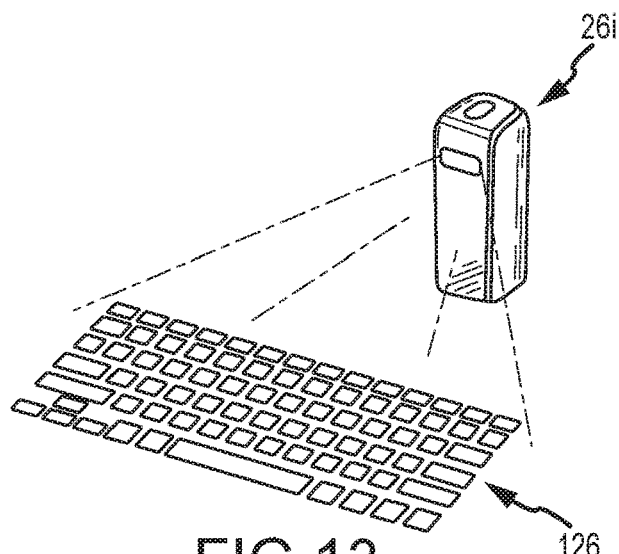

FIGS. 12-13 are diagrammatic views of eighth and ninth embodiments of the bedside interface device comprising holographic mouse and keyboard input devices, respectively. Holographic mouse 26h deploys light beam pattern 124, which is used by the mouse 26h to acquire user input (i.e., movement of the physician's finger, instead of moving a conventional mouse). The movement input can be used in the same manner as that obtained from a conventional mouse. Holographic keyboard 26i also deploys a light beam pattern 126 corresponding to a keyboard. A physician's finger can be used to "select" the key much in the same manner as a conventional keyboard, but without any physical contact. Devices 26h, 26i have the advantage of being sterile without any disposables, and can incorporate wireless communications and may be powered using batteries (i.e., no cables needed).

It should be understood that variations are possible. For example, in a further embodiment, primary control by the physician in manipulating or interacting with the mapping system may be through use of voice control alone (i.e., a microphone coupled with voice recognition logic), apart from its inclusion with other modes or devices for user interaction described above. In a still further embodiment, the physician can be equipped with headgear that monitors head movements to determine at what location on the screen/monitor the physician is looking. In effect, such headgear can act as a trackball to move or otherwise manipulate an image (or view of a model) on the monitor in accordance with the physician's head movements. In a yet further embodiment, the physician can be equipped with headgear that monitors head movements and/or also monitors brainwave patterns (e.g., to record a user electroencephalogram (EEG)). Such monitored data can be analyzed to derive or infer user input or commands for controlling an image (or view of a model), as described above. An EEG-based embodiment may comprise conventional apparatus known in the art, for example, commercially available products respectively sold under the trade designation MindWave™ headset from NeuroSky, Inc., San Jose, Calif., USA, or the Emotiv EPOC™ personal interface neuroheadset from Emotiv, Kwun Tong, Hong Kong. In a still further embodiment, the physician can be equipped with an eye tracking apparatus, wherein monitored eye movements constitute the user input to be interpreted by the system (e.g., the eye movements can be interpreted as a cursor movement or other command).

It should also be appreciated that while the foregoing description pertains to an EP physician manually controlling a catheter through the use of a manually-actuated handle or the like, other configurations are possible, such as robotically-actuated embodiments. For example, a catheter movement controller (not shown) described above may be incorporated into a larger robotic catheter guidance and control system, for example, as seen by reference to U.S. application Ser. No. 12/751,843, filed 31 Mar. 2010, which is hereby incorporated by reference as though fully set forth herein. Such a robotic catheter system may be configured to manipulate and maneuver catheters within a lumen or a cavity of a human body, while the bedside interface devices described herein can be used to access and control the EP diagnostic and/or therapeutic systems. In at least one embodiment, a bedside interface device as described herein may also be used to access and control the robotic catheter system.

Figure 14:
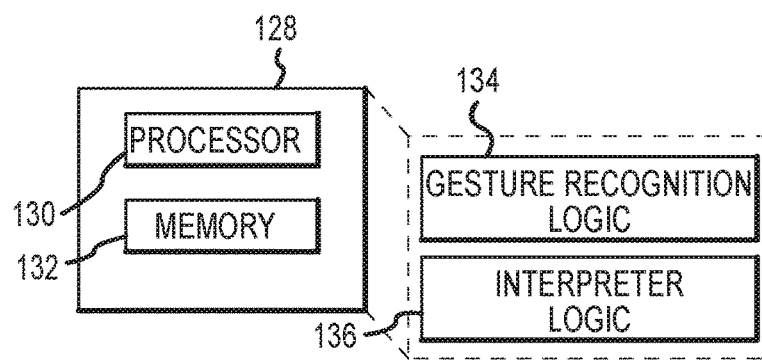
FIG. 14 is a block diagram of an embodiment of a base interface used in connection with a system for enabling a user to control a robotic catheter system.

FIG. 14 is a block diagram of a base interface, designated 128, which may be one part of a system 127 (FIG. 15) configured to enable one or more users to remotely control a robotic medical device system, such as a robotic catheter system. In an embodiment, another part of system 127 may comprise a motion capture apparatus, for example, motion capture apparatus 26d shown in FIG. 15. Motion capture apparatus 26d may be configured to capture the motion of one or more users in a sensing volume and generate output data indicative of the captured user motion. Base interface 128 may be configured generally to analyze the generated output data from the motion capture apparatus 26d to identify/recognize one or more three-dimensional (3D) gestures, and then translate such gestures into one or more robotic catheter control commands. The catheter control commands may be configured to control an aspect of the operation of the robotic catheter system. One such robotic catheter system is described in connection with FIGS. 18-23.

With continued reference to FIG. 14, base interface 128 includes an electronic control unit having one or more electronic processors 130 and memory 132. Base interface 128 further includes gesture recognition logic 134 and interpreter logic 136. Both gesture recognition logic 134 and interpreter logic 136, in an embodiment, comprise programmed logic (e.g., software) that is stored in memory 132 and is configured to be executed by the one or more processors 130.

Gesture recognition logic 134 is configured to recognize one or more three-dimensional (3D) user gestures based on an analysis of the output data generated by motion capture apparatus 26d. In an embodiment, motion capture apparatus 26d comprises commercially available components, for example, the Kinect™ game control system, available from Microsoft, Redmond, Wash., USA. Gesture recognition logic 134 can, in an embodiment, comprise implementations developed using a Kinect™ software development kit (SDK), which includes drivers, rich application programming interfaces (API's), among other things, that enables access to the capabilities of the Kinect™ device. The SDK allows access to raw sensor streams (e.g., depth sensor, color camera sensor, and four-element microphone array), skeletal tracking, advanced audio (i.e., integration with Windows speech recognition) as well as other features.

Interpreter logic 136 is configured to translate the one or more 3D gestures recognized by gesture recognition logic 134 to one or more corresponding robotic catheter control commands. Such robotic catheter control commands may be configured to control one or more aspects of the operation of a robotic catheter system, such as the robotic catheter system described in connection with FIGS. 18-23. For example only, such commands can include deflection, rotation, and/or translation of one or more robotically controlled catheters and/or sheaths. Interpreter logic 136, in an embodiment, may comprise application level code configured to use, for example, various features available in the Kinect™ SDK mentioned above.

FIG. 15 is a diagrammatic and block diagram view of system 127, which includes motion capture apparatus 26d and base interface 128. In at least one embodiment, motion capture apparatus 26d includes capture apparatus 116 having both optical sub-system 118 and microphone sub-system 120, as described above in connection with FIG. 8. Motion capture apparatus 26d may be configured to detect (e.g., optically) the physical motion of various objects, such as a user including portions of the user such as fingers, hands, arms, etc., that occur within a sensing volume 122. The detected physical motion can also be that of a user-controlled implement, such as a wand (e.g., part or all of electronic wand system 26b described above) or the like. In an embodiment, sensing volume 122 is located proximate to the motion capture apparatus 26d. Motion capture apparatus 26d may be electrically connected to base interface 128 for communication thereto of user motion data.

The user motion data is indicative of the captured user motion. The user motion data may include imaging data as well as other information concerning the 3D posture of various objects in the sensing volume. In this regard, it should be appreciated that as updates occur over time, the resulting time-based series can be used to determine the motion patterns of the objects being tracked. Base interface 128 may be coupled to a robotic catheter system such as robotic control system 210, as shown, over a communication mechanism 46, as also described above.

In an embodiment, gesture recognition logic 134 (FIG. 14) is configured to track an object, for example, a specific body part such as a user's hand. Motion capture apparatus 26d can define the tracked object by one or more fiducial points. For example, in an embodiment, motion capture apparatus 26d, in combination with software functionality as implemented in base interface 128 (e.g., via the SDK), can recognize and track the time-based motion of a person's body or skeleton 138, including the time-based tracking of one or more of a plurality of constituent joints $140_1$, $140_2$, ... $140_n$, where n is an integer. The above-mentioned fiducial points may be taken to correspond to the joints $140_1$, $140_2$, ... $140_n$. Gesture recognition logic 134 can track the time-based positions of these fiducial points. The tracked positions in turn can form the basis of various metrics, such as position, distance, and rotation, all to be described below.

In light of the above, the output data generated by motion capture apparatus 26d includes fiducial point tracking data associated with a plurality of fiducial points defined with respect to the user. The fiducial point tracking data includes, for each fiducial point, a respective position. Each position may include a respective three-dimensional coordinate in a reference coordinate system, for example, defined within sensing volume 122 that is monitored by motion capture apparatus 26d. In addition and/or in the alternative, the output motion data generated by motion capture apparatus 26d may comprise imaging data.

As shown in FIG. 16A, for example, a skeleton 138a shows the respective positions of two fiducial points at $140_3$ and $140_4$ corresponding to the separated hands of the user. Gesture recognition logic 134 is configured to determine the position of the user's hands, and also a distance 142 between the user's hands. The position and distance between the user's hands can be translated by interpreter logic 136 to a robotic catheter control command. For example, the position and distance between the user's hands can be used to control the degree of extension or retraction of a catheter and/or a sheath along a respective translation axis. Thus, more generally, a robotic catheter control command may have a characteristic that corresponds to the magnitude of the action that is to be initiated by the command. In the example of FIG. 16A, the magnitude of the action may be defined by the distance between preselected fiducial points. The action may be a catheter extension, a catheter retraction, a sheath extension, and a sheath retraction.

As shown in FIG. 16B, as a further example, a skeleton 138b shows a sequence of time-based positions traversed by a single fiducial point (joint $140_4$) during the rotation of a user's wrist. The time-based positions of the tracked fiducial point (joint $140_4$) at times $t_1$, $t_2$, $t_3$, $t_4$ and $t_5$ are designated $140_{4\text{-}1}$, $140_{4\text{-}2}$, $140_{4\text{-}3}$, $140_{4\text{-}4}$, and $140_{4\text{-}5}$ respectively. Through tracking, gesture recognition logic 134 can determine the extent of the rotation, as indicated by rotation angle 144. In an embodiment, gesture recognition logic 134 recognizes the rotational motion while interpreter logic 136 translates this gesture into an output command, for example only, to actuate rotation of a catheter and/or a sheath. Interpreter logic 136 can be configured to generate the output rotation command further as a function of the determined rotation angle 144 (i.e., the extent of actual catheter and/or sheath rotation can be made to correspond to the determined rotation angle 144). The fiducial point tracking data output from motion capture apparatus 26d therefore includes, for each fiducial point, a respective time-based plurality of positions. Thus, more generally, a robotic catheter control command may have a characteristic that corresponds to the rotation associated with the action to be initiated by the command. In the example of FIG. 16B, the rotation may be defined by the rotation angle through which the preselected fiducial point rotates. The action may be a catheter or sheath rotation.

In an embodiment, in the case of a gesture involving wrist rotation, gesture recognition logic 134 can be additionally configured to identify and track a wand (e.g., part or all of electronic wand system 26b described above), a baton or a like implement being held in the hand of the user. The use of such implements can improve the ability of the motion capture apparatus 26d to track the user's wrist motion (rotation). For example, a wand, being generally larger and more distinct than a wrist fiducial point (joint), can be expected to provide a correspondingly larger object in the imaging data and/or other data provided by the motion capture apparatus 26d. This effectively provides greater resolution and robustness in the tracking functionality of motion capture apparatus 26d/gesture recognition logic 134.

Gesture recognition logic 134 may be configured to operate as described below to recognize a 3D gesture. First, gesture recognition logic 134 is configured to identify a start pose based on the fiducial point tracking data. In an embodiment, the start pose may correspond to a start condition where a first set of fiducial points assumes a first relationship therebetween. For example, this condition may be satisfied when the fiducial points form a first predetermined "constellation". Second, gesture recognition logic 134 is configured to record the motion of a predetermined plurality of fiducial points after recognition of the start pose, and continue recording until an end pose is identified, which identification is also based on the fiducial tracking data. In an embodiment, the end pose may correspond to an end condition where a second set of fiducial points assume a second relationship therebetween. For example, this condition may be satisfied when the fiducial points form a second predetermined "constellation".

Third, gesture recognition logic 134 is configured to compare the recorded motion of the predetermined plurality of fiducial points (being tracked) with a plurality of predefined gestures. Each predefined gesture is itself defined by a respective motion of a respective set of fiducial points. Finally, gesture recognition logic 134 is configured to output one of the plurality of predefined gestures as the recognized gesture when the recorded motion matches one of the predefined gestures (i.e., the recognized gesture being the one that matches the recorded motion).

System 127 may also include various safety features. As described above, motion capture apparatus 26*d* is generally responsive to activity occurring within sensing volume 122. In an embodiment, motion capture apparatus 26*d*/gesture recognition logic 134 can be configured to be responsive only to activity in a smaller 3D volume included within sensing volume 122 (hereinafter an "action box"). The purpose of the action box is that once it is defined, system 127 will only respond to actions that occur within the action box. For example, a user can only actuate the robotic catheter system by placing his hands in the action box or otherwise causing some activity to occur in the action box. This arrangement can be expected to reduce the occurrence of unintended actuation, thereby improving safety. The action box of sensing volume 122 can be positioned above a patient table (see FIG. 2, which shows a patient table and patient), in a control room, for example, control area/room 12 in FIG. 1, or in various other locations.

In an embodiment, system 127 can be configured to allow the user to adjust either or both of the size and location of the action box relative to motion capture apparatus 26*d*. It should be understood that motion capture apparatus 26*d* will only respond to activities occurring within the action box, and ignore all other activity outside the action box. Staff can be trained to never place their hands or any other object into the action box as it is strictly for use by a trained physician because of the potential to actuate functionality of a medical device. In this regard, the action box can be delineated by a visible construct, such as a frame. The frame can be made of solid material, in which case is also presents a physical construct, or the outlines of the frame can be illuminated, for example, via low intensity laser beams.

For additional safety protection, system 127 can be configured to include a user-actuatable switch such as a deadman switch 146. Switch 146 may include a normally open state and a user-actuatable closed state. System 127 can be configured to be active only when the dead-man switch 146 has been closed by the user. System 127 may only respond to user actions (gestures) when the switch 146 has been actuated. In a further embodiment, system 127 may be configured to at least disable communication of a robotic control command to the robotic catheter system unless switch 146 is in the closed state. The dead-man switch 146 may comprise a switch on a wand, a foot pedal, or the like.

Although an embodiment has been described in connection with FIGS. 14-15 and FIGS. 16A-16B, other motion capture mechanisms can be used. For example, alternatives include an optical-based position tracking product (e.g., object or fiducial tracking system) known by the trade designation as the POLARIS® system and a magnetic-field based product known by the trade designation as the AURORA® system, both from Northern Digital Inc.

Figure 17:
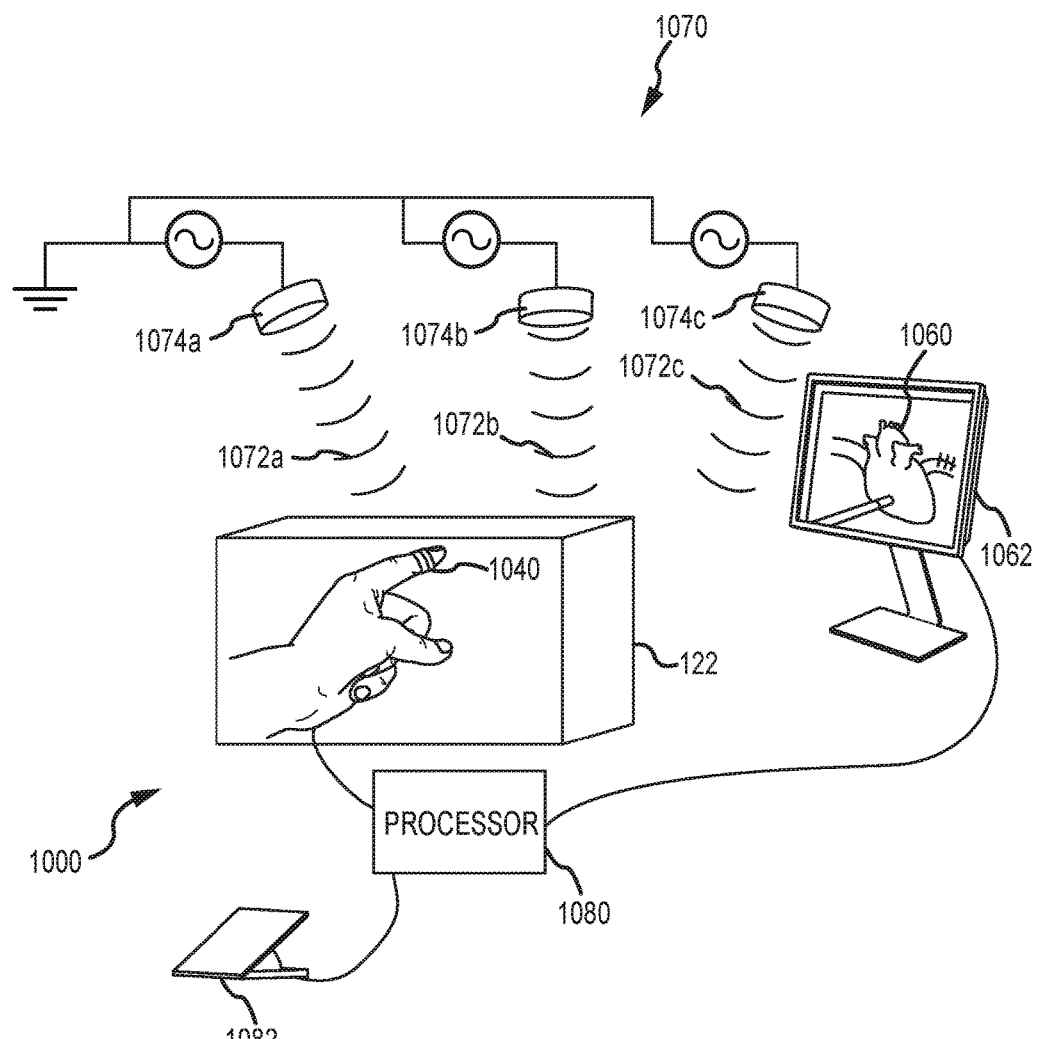
FIG. 17 is an exemplary illustration of a three dimensional input device usable with a robotic catheter system.

FIG. 17 shows a further embodiment involving hand motion tracking where a user input device 1000 can include a spatially detected glove or stylus. In an embodiment where user input device 1000 includes a spatially detected glove, the user's/wearer's index finger can be instrumented with various sensors 1040 (e.g., position and orientation sensors, and/or accelerometers). The glove or stylus input device can be locatable in 3-D space through the use of a positioning system employing a magnetic field, an electrostatic field, or through the use of an optical positioning system. In an embodiment, the positioning system can be implemented within a liquid tank (e.g., water tank), where field generators, such as those associated with the EnSite™ NavX™ control system (a product of St. Jude Medical), are externally attached. For such embodiments, an instrumented glove or stylus can extend into the tank while, for example, the user's finger (e.g., index finger), or stylus can be instrumented with electrodes configured to measure parameters of the electric field. In an embodiment, the construction and/or placement of the sensors (e.g., EnSite™ NavX™-type electrodes) can be similar to sensors on the distal portion of the catheter. In another embodiment, the positioning system can be implemented using a magnetic positioning system.

In the illustrated embodiment of FIG. 17, a magnetic positioning system 1070 can operate, for example, by emitting several magnetic fields 1072*a*-1074*c* from an array of field generators 1074*a*-1074*c*. Sensor coils (e.g., sensors 1040 or 1052) located on the glove or stylus can then sense the magnetic field strength emanating from each sensor coil. By selectively energizing each field generator at a different time or frequency, a processor 1080 can be able to resolve the sensor's position and orientation relative to each field generator or to a fixed reference sensor. Detected changes in the position and orientation of the glove or stylus sensor can then be registered and user motion data can be determined, and passed on to gesture recognition logic 134.

In a still further embodiment, a haptic glove (not shown) with sensors can be provided in order to capture user motion, to thereby allow recognition of user gestures, as seen by reference to U.S. application Ser. No. 12/507,175, filed 22 Jul. 2009 (published as United States patent application publication no. US 2010/0073150 A1), and hereby incorporated by reference as though fully set forth herein. A haptic glove can output data that allows detection of the relative bending of the fingers and joints within the hand. Various motions of the hand can be indicators of desired motion to be input into the robotic catheter system. A haptic glove or similar devices have the potential to detect motion relative to itself, but not absolute motion relative to the physical (real) world. In an embodiment and referring again to FIGS. 14-15, a hybrid motion capture system is provided, wherein a haptic glove is configured to simultaneously provide relative motion such as finger bending as described above combined with an absolute location device, such as motion capture apparatus 26*d*, to form composite motions or gestures (using input from both systems). Such composite motions can be provided to gesture recognition logic 134 and interpreter logic 136 to output corresponding robotic catheter control commands, for effecting precise motions of the catheter and/or sheath of the robotic catheter system.

As described above, user-provided gestures can also be captured and used to control other electrophysiological systems, such an electro-anatomic mapping and visualization system (e.g., an EnSite™ Velocity™ system). In the scenario where user gesture capture is contemplated for controlling multiple, different systems, such as the robotic catheter system and the Ensite™ Velocity™ system, system 127 can be configured with context switching functionality. In other words, system 127 is configured to determine when a gesture is intended to control one target system such as the robotic catheter system versus another target system such as an electro-anatomic mapping and visualization system.

To facilitate making such determinations, system 127 is configured to analyze the actions occurring within a context switching box 148, shown in FIG. 15. As illustrated, context switching box 148 may be located near the corner of sensing volume 122. In an embodiment, system 127 is configured to detect when the user is "tapping" in context switching box 148. Thus, when the user "taps" a point in context switching box 148, system 127 switches context (i.e., from the robotic catheter system as the target to the mapping system as the target) and thereafter allows user input to control an electro-anatomic mapping system target, such as the Ensite™ Velocity™ system. The act of tapping may involve the user holding his or her hand in a particular location and then ballistically moving the fingers back and forth. This tapping motion, when detected by gesture recognition logic 134, causes an electro-anatomic system, such as system 34—FIG. 2, to display a context menu visible to the user. For example, such a context menu may have a series of selectable options in a "drop-down" style box.

In operation, the user, by moving the hand up and/or down "over" the selectable options, causes the option over which the hand hovers to become highlighted. Gesture recognition logic 134 can be further configured to recognize a second tapping motion, which finalizes the selection and closes the context menu. While the gesture itself can be captured using system 127, other detection mechanisms, such as through the use of various sensors as described above (e.g., haptic glove, accelerometer disposed within a glove, a wand, etc.) can be alternatively used.

Thus, in light of the above, system 127 may include context switching logic (not shown) stored in memory 132 and configured for execution in the one or more processors 130. The context switching logic may be configured to detect a predetermined context switching gesture (e.g., the "tapping" gesture described above) based on the output data from motion capture apparatus 26d, but only where the context switching gesture occurs in the context switching portion of sensing volume 122. When the context switching logic detects the context switching gesture, it may set a context switch parameter or the like. Interpreter logic 136 is accordingly configured to selectively translate, based on the state of the context switch parameter, the recognized user gesture into one of either (i) a robotic catheter control command, or (ii) an electro-anatomic mapping system control command.

In another embodiment, further visual feedback can be displayed on the display of the electro-anatomic system 34, such as on the display area 52 in FIG. 2, showing the relative motion of the user's hands and fingers. This feedback can be through the use of a (i) special-purpose mouse pointer in addition to and visibly distinguishable from a primary mouse pointer, (ii) a graphical representation of the hands, or the like.

Referring to FIG. 15, in another embodiment, system 127 can be used in combination with an electro-anatomic system 34 (FIG. 2) and further in combination with a three-dimensional (3D) display, such as that described in U.S. application No. 61/643,667, filed 7 May 2012, and hereby incorporated by reference as though fully set forth herein. This combination of functions allows for a virtual representation of the hands that could be rendered and displayed within a three-dimensional (3D) window along with representations of the catheters and/or sheaths, all with respect to a heart model. This 3D window may allow the user to perceive his or her own hands reaching into the heart of the patient. Through this facility, the user could "grab" the catheter and move it to a new location, for example, to a target location. For example, the virtual hands can be moved near the tip of one of the catheters, and by "pinching" on the tip of the catheter, the user can "grab and pull" the catheter in different directions. The target location can be specified as the location to which the rendered catheter is pulled by the user. Once the target location has been specified, this information can be passed on to the robotic control system 210 by interpreter logic 136, wherein robotic control system 210 processes this target location as a dynamic waypoint, and thereafter automatically move the catheter to such target location. The foregoing combination, including a 3D display, provides an intuitive way for a user to manipulate a medical device within the heart.

In another embodiment, interpreter logic 136 can be configured to generate different commands based on the same user gesture. Interpreter logic 136 is configured to analyze the recognized use gesture in light of and as a function of the orientation of the then-visible (current) view of an anatomical model being displayed by an electro-anatomic system, such as system 34 (FIG. 2). In other words, the effect of the user gesture can be view relative, such that the same gesture can actuate different, relative motions based on the current view angle or orientation displayed by the electro-anatomic system 34. For example, the direction of translation can be different based on the current view, as shown in the examples in Table 1,

TABLE 1

View relative actions versus gestures

| GESTURE | VIEW | ACTION |
| --- | --- | --- |
| Hand moves right-to-left | anteroposterior (AP) view, with catheter distal tip pointing left on the screen. | Advance |
| Hand moves right-to-left | posteroanterior (PA) | Retract |

Exemplary RCGS System Description.

Figure 18:
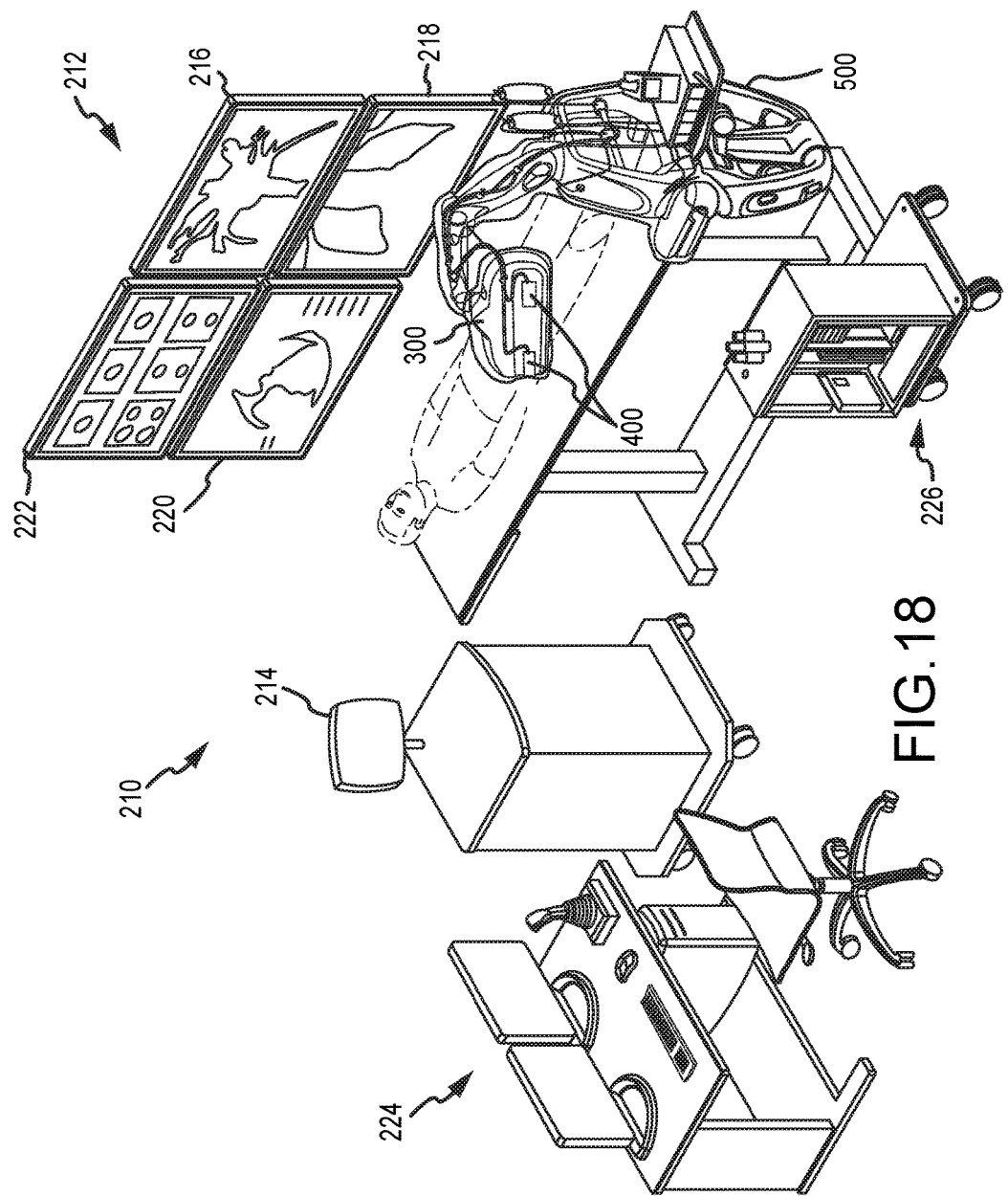
FIG. 18 is an isometric, diagrammatic view of a robotic catheter system, illustrating an exemplary layout of various system components.

Referring to FIG. 18, RCGS 210 can be likened to power steering for a catheter system. The RCGS 210 can be used, for example, to manipulate the location and orientation of catheters and sheaths in a heart chamber or in another body cavity or lumen. The RCGS 210 thus provides the user with a similar type of control provided by a conventional manually-operated system, but allows for repeatable, precise, and dynamic movements. For example, a user such as an electrophysiologist can identify locations (potentially forming a path) on a rendered computer model of the cardiac anatomy. The system can be configured to relate those digitally selected points to positions within a patient's actual/physical anatomy, and can thereafter command and control the movement of the catheter to the defined positions. Once at the specified target location, either the user or the system can perform the desired diagnostic or therapeutic function. The RCGS 210 enables full robotic navigation/guidance and control.

As shown in FIG. 18, the RCGS 210 can generally include one or more monitors or displays 212, a visualization, mapping and navigation (including localization) system 214, a human input device and control system (referred to as "input control system") 224, an electronic control system 226, a manipulator assembly 300 for operating a device cartridge 400, and a manipulator support structure 500 for positioning the manipulator assembly 300 in proximity to a patient or a patient's bed.

Displays 212 are configured to visually present to a user information regarding patient anatomy, medical device location or the like, originating from a variety of different sources. Displays 212 can include (1) an EnSite™ Velocity™ monitor 216 (coupled to system 214—described more fully below) for displaying cardiac chamber geometries or models, displaying activation timing and voltage data to identify arrhythmias, and for facilitating guidance of catheter movement; (2) a fluoroscopy monitor 218 for displaying a real-time x-ray image or for assisting a physician with catheter movement; (3) an intra-cardiac echo (ICE) display 220 to provide further imaging; and (4) an EP recording system display 222.

The system 214 is configured to provide many advanced features, such as visualization, mapping, navigation support and positioning (i.e., determine a position and orientation (P&O) of a sensor-equipped medical device, for example, a P&O of a distal tip portion of a catheter). Such functionality can be provided as part of a larger visualization, mapping and navigation system, for example, an EnSite™ Velocity™ system running a version of EnSite™ NavX™ software commercially available from St. Jude Medical, Inc., of St. Paul, Minn. and as described above. System 214 can thus comprise conventional apparatus, for example, the EnSite™ Velocity™ system, or other known technologies for locating/navigating a catheter in space (and for visualization), including for example, the CARTO visualization and location system of Biosense Webster, Inc., the AURORA® system of Northern Digital Inc., a magnetic field based localization system such as the MediGuide™ Technology, a system based on technology from MediGuide Ltd. of Haifa, Israel and now owned by St. Jude Medical, Inc., or a hybrid magnetic field-impedance based system, such as the CARTO 3 visualization and location system of Biosense Webster, Inc. Some of the localization, navigation and/or visualization systems can involve providing a sensor for producing signals indicative of catheter location and/or orientation information, and can include, for example one or more electrodes in the case of an impedance-based localization system such as the EnSite™ Velocity™ system running EnSite™ NavX™ software, which electrodes can already exist in some instances, or alternatively, one or more coils (i.e., wire windings) configured to detect one or more characteristics of a low-strength magnetic field, for example, in the case of a magnetic-field based localization system such as the MediGuide™ Technology, a system using technology from MediGuide Ltd. described above.

The input control system 224 is configured to allow a user, such as an electrophysiologist, to interact with the RCGS 210, in order to control the movement and advancement/withdrawal of both a catheter and sheath (see, e.g., U.S. application Ser. No. 12/751,843, filed 31 Mar. 2010 (the '843 application), and PCT/US2009/038597, filed 27 Mar. 2009 (the '597 application), and published 1 Oct. 2009 under publication no. WO 2009/120982. The '843 application and the '597 application are both hereby incorporated by reference as though fully set forth herein. Generally, several types of input devices and related controls can be employed, including, without limitation, instrumented traditional catheter handle controls, oversized catheter models, instrumented user-wearable gloves, touch screen display monitors, 2-D input devices, 3-D input devices, spatially detected styluses, and traditional joysticks. For a further description of exemplary input apparatus and related controls, see, for example, U.S. application Ser. No. 12/933,063, filed 16 Sep. 2010 (the '063 application), and U.S. application Ser. No. 12/347,442, filed 31 Dec. 2008 (the '442 application). The '063 application and the '442 application are both hereby incorporated by reference as though fully set forth herein. The input devices can be configured to directly control the movement of the catheter and sheath, or can be configured, for example, to manipulate a target or cursor on an associated display.

The electronic control system 226 is configured to translate (i.e., interpret) inputs (e.g., motions) of the user at an input device or from another source into a resulting movement of the catheter and/or surrounding sheath. In this regard, the system 226 includes a programmed electronic control unit (ECU) in communication with a memory or other computer readable media (memory) suitable for information storage. Relevant to the present disclosure, the electronic control system 226 is configured, among other things, to issue commands (i.e., actuation control signals) to the manipulator assembly 300 (i.e., to the actuation units—electric motors) to move or bend the catheter and/or sheath to prescribed positions and/or in prescribed ways, all in accordance with the received user input and a predetermined operating strategy programmed into the system 226. In addition to the instant description, further details of a programmed electronic control system can be found in U.S. application Ser. No. 12/751,843, described above. It should be understood that although the exemplary EnSite™ Velocity™ system 214 and the electronic control system 226 are shown separately, integration of one or more computing functions can result in a system including an ECU on which can be run both (i) various control and diagnostic logic pertaining to the RCGS 210 and (ii) the visualization, mapping and navigation functionality of system 214.

The manipulator assembly 300, in response to such commands, is configured to maneuver the medical device (e.g., translation movement, such as advancement and withdrawal of the catheter and/or sheath), as well as to effectuate distal end (tip) deflection and/or rotation or virtual rotation. In an embodiment, the manipulator assembly 300 can include actuation mechanisms/units (e.g., a plurality of electric motor and lead screw combinations, or other electric motor configurations, as detailed below) for linearly actuating one or more control members (e.g., steering wires) associated with the medical device for achieving the above-described translation, deflection and/or rotation (or virtual rotation). In addition to the description set forth herein, further details of a manipulator assembly can be found in U.S. application Ser. No. 12/347,826, filed 31 Dec. 2008, which is hereby incorporated by reference as though fully set forth herein. Although the manipulator 300 is illustrated and described with respect to the manipulation of a single medical device (e.g., a single catheter and sheath combination), the manipulator 300 can be configured to manipulate multiple devices, such as a cardiac mapping catheter, an ablation catheter, an imaging catheter, such an intracardiac echocardiography (ICE) catheter, or the like, as seen by reference to international application no. PCT/US12/30697, with an international filing date of 27 Mar. 2012 (the '697 application), which claims priority to U.S. provisional application No. 61/581,838 filed 30 Dec. 2011 (the '838 application). The '697 application and the '838 application are both hereby incorporated by reference as though fully set forth herein.

A device cartridge 400 is provided for each medical device controlled by the RCGS 210. For this exemplary description of an RCGS, one cartridge is associated with a catheter and a second cartridge is associated with an outer sheath. The cartridge is then coupled, generally speaking, to the RCGS 210 for subsequent robotically-controlled movement. In addition to the description set forth herein, further details of a device cartridge can be found in U.S. application Ser. No. 12/347,835, filed 31 Dec. 2008 (the '835 application), and U.S. application Ser. No. 12/347,842, filed 31 Dec. 2008 (the '842 application). The '835 application and the '842 application are both hereby incorporated by reference as though fully set forth herein.

Figure 19:
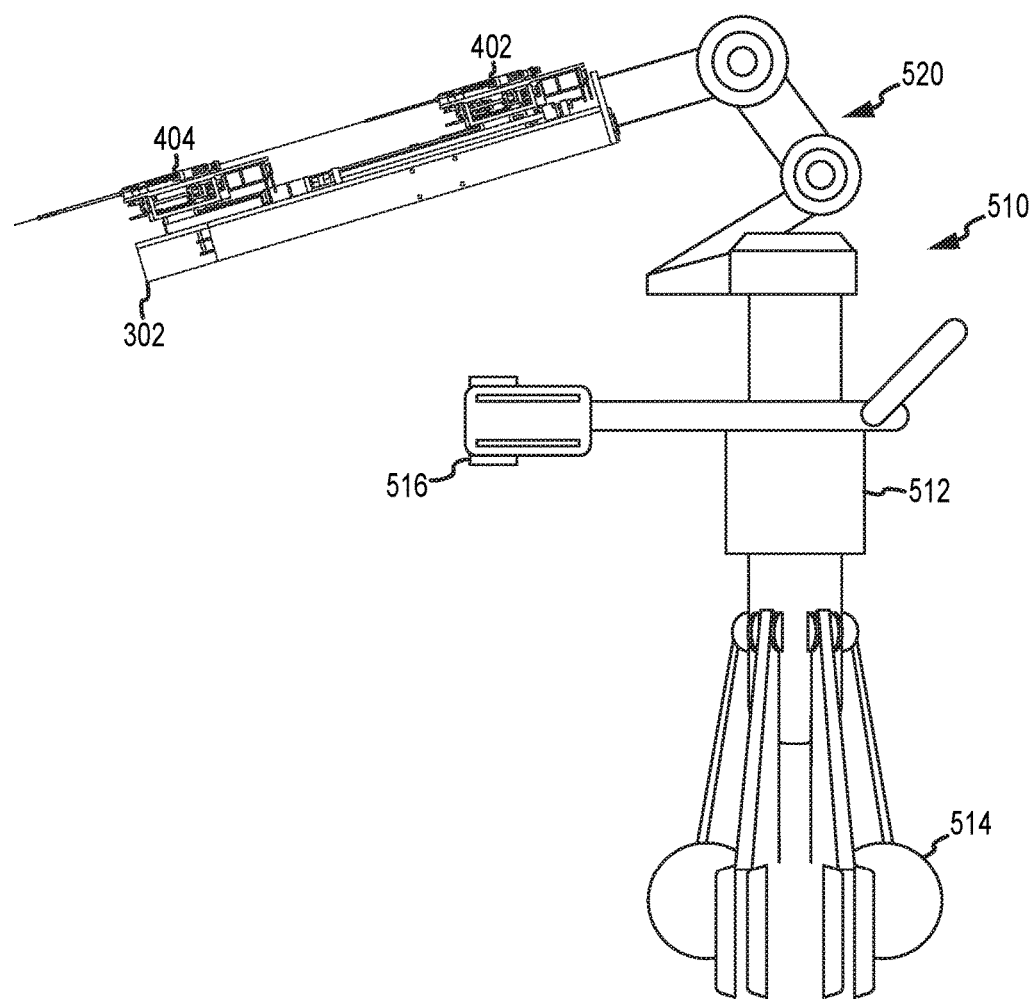
FIG. 19 is a side view of a manipulator assembly shown in FIG. 18, coupled to a robotic support structure, showing side views of catheter and sheath manipulation mechanisms.

FIG. 19 is a side view of an exemplary robotic catheter manipulator support structure, designated structure 510 (see U.S. application Ser. No. 12/347,811, filed 31 Dec. 2008, hereby incorporated by reference as though fully set forth herein). The structure 510 can generally include a support frame 512 including retractable wheels 514 and attachment assembly 516 for attachment to an operating bed (not shown). A plurality of support linkages 520 can be provided for accurately positioning one or more manipulator assemblies, such as manipulator assembly 302. The assembly 302 is configured to serve as the interface for the mechanical control of the movements or actions of one or more device cartridges, such as catheter and sheath cartridges 402, 404 described below. Each device cartridge is configured to receive and retain a respective proximal end of an associated medical device (e.g., catheter or sheath). The assembly 302 also includes a plurality of manipulation bases onto which the device cartridges are mounted. After mounting, the manipulator assembly 302, through the manipulation bases, is capable of manipulating the attached catheter and sheath.

Figure 20A:
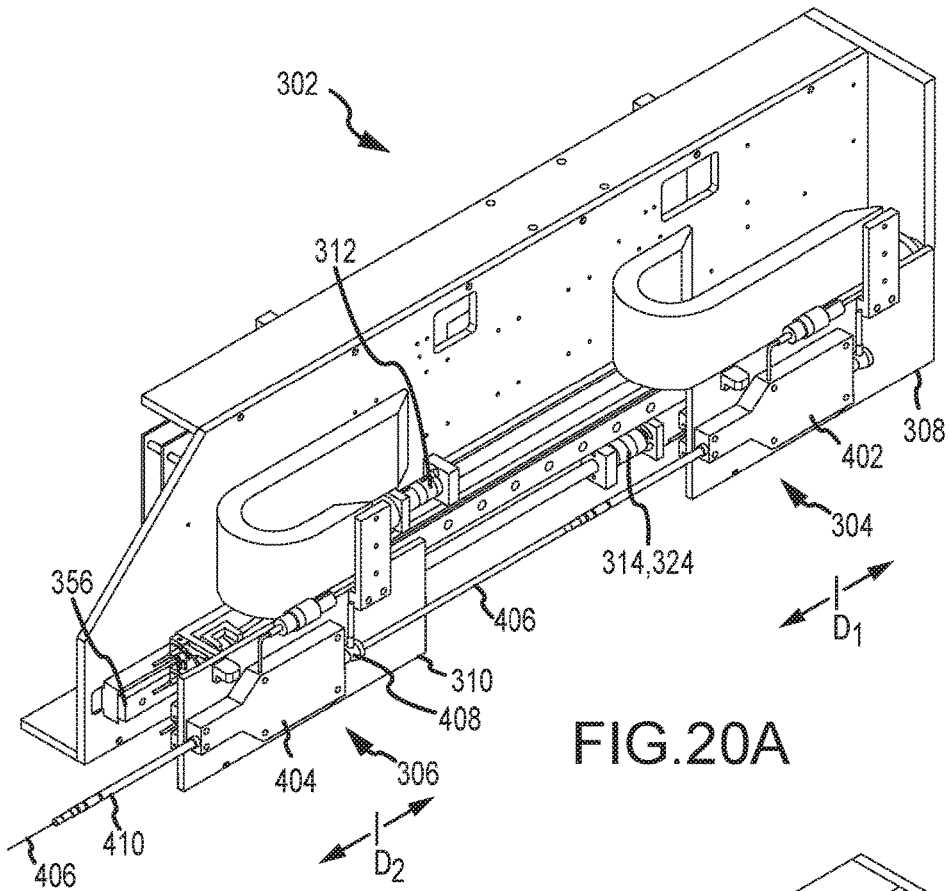
FIGS. 20A-20B are isometric views of a manipulator assembly shown in FIG. 19, showing the catheter and sheath manipulation mechanism in greater detail.
Figure 20B:
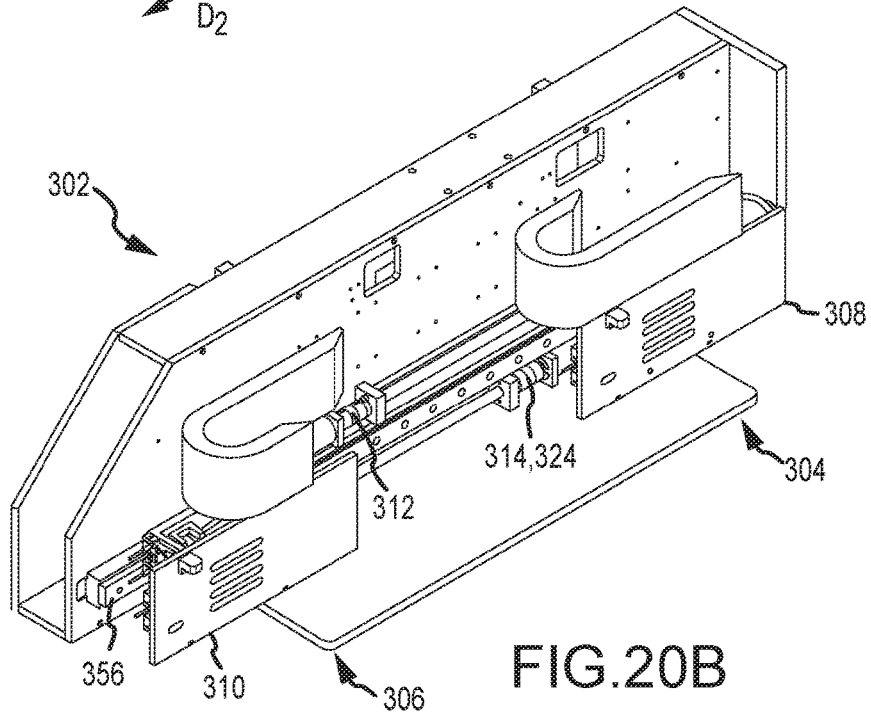
Figure 21A:
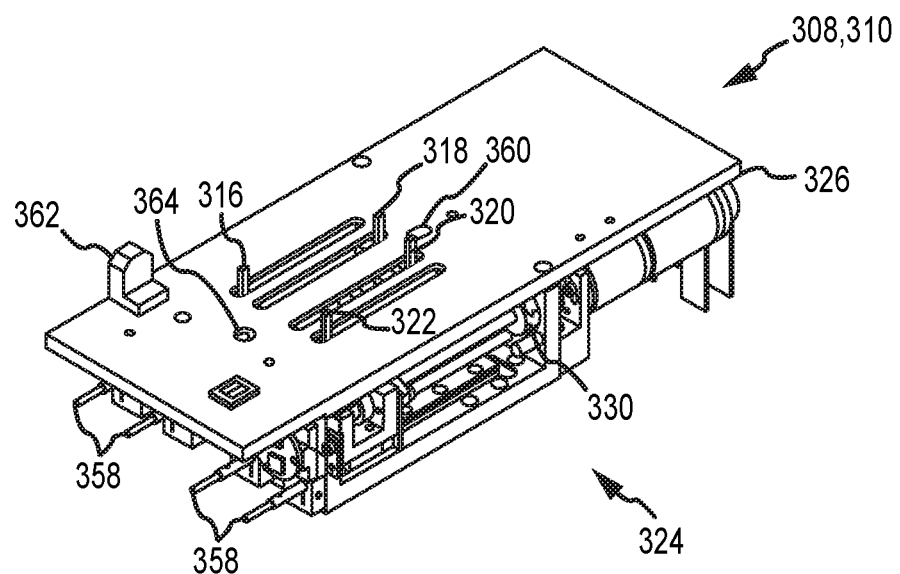
FIGS. 21A-21C are isometric views showing a sheath manipulation base of FIGS. 20A-20B in greater detail.
Figure 21B:
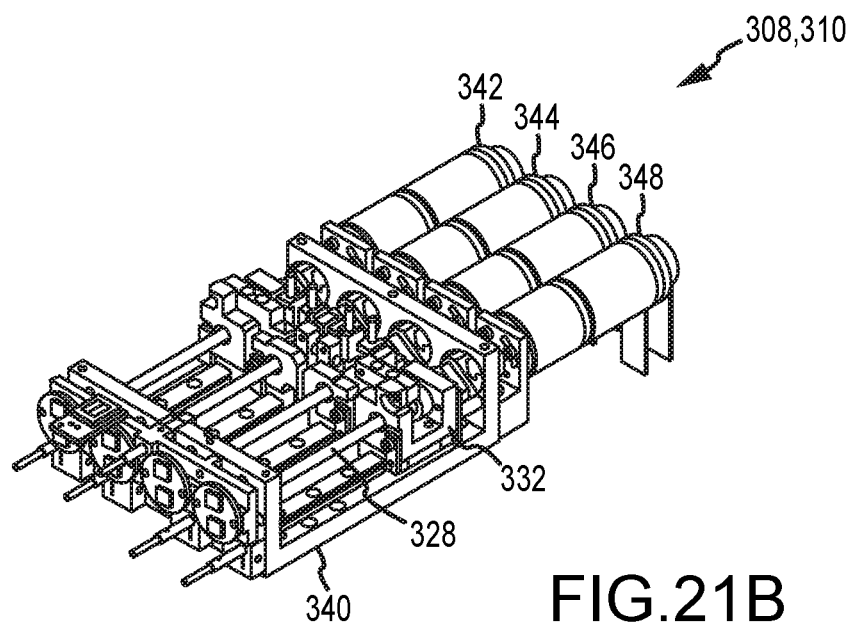
Figure 21C:
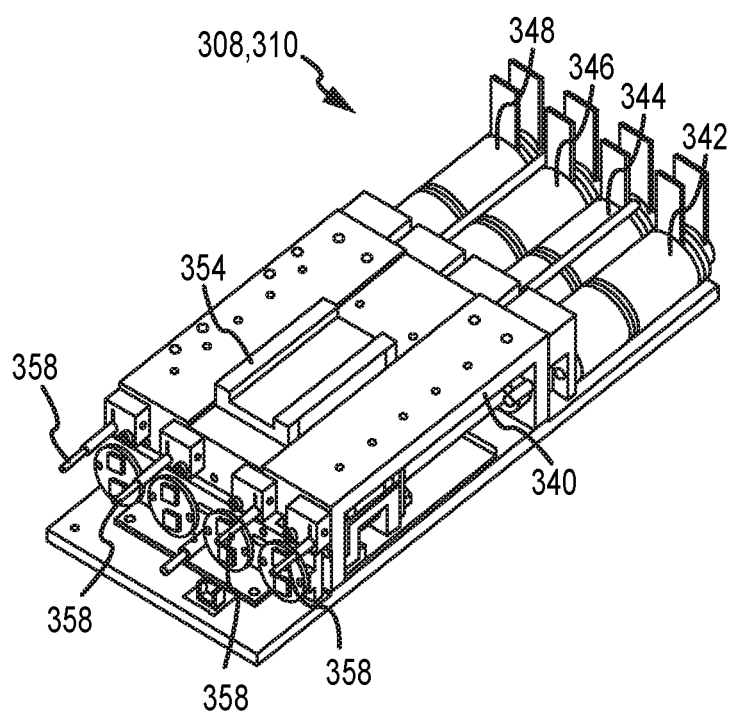
Figure 22A:
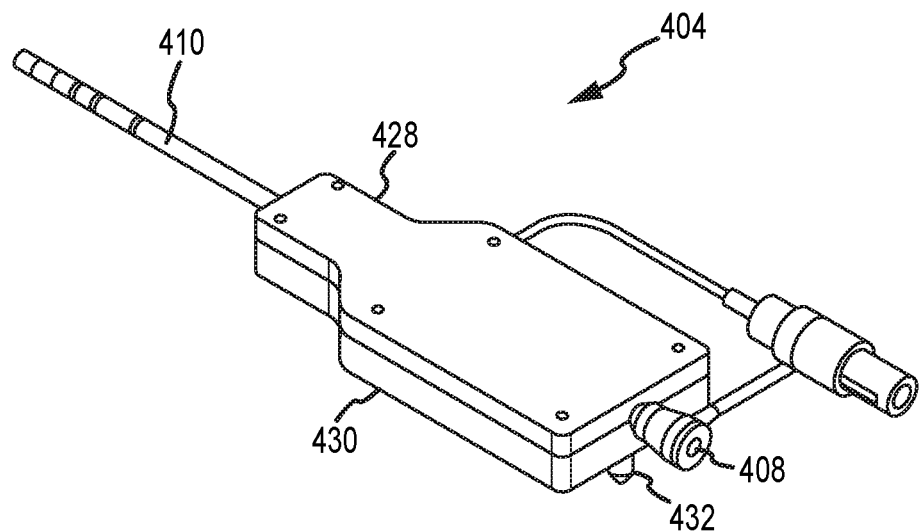
FIGS. 22A-22B are isometric views showing a sheath cartridge of FIGS. 20A-20B in greater detail.
Figure 22B:
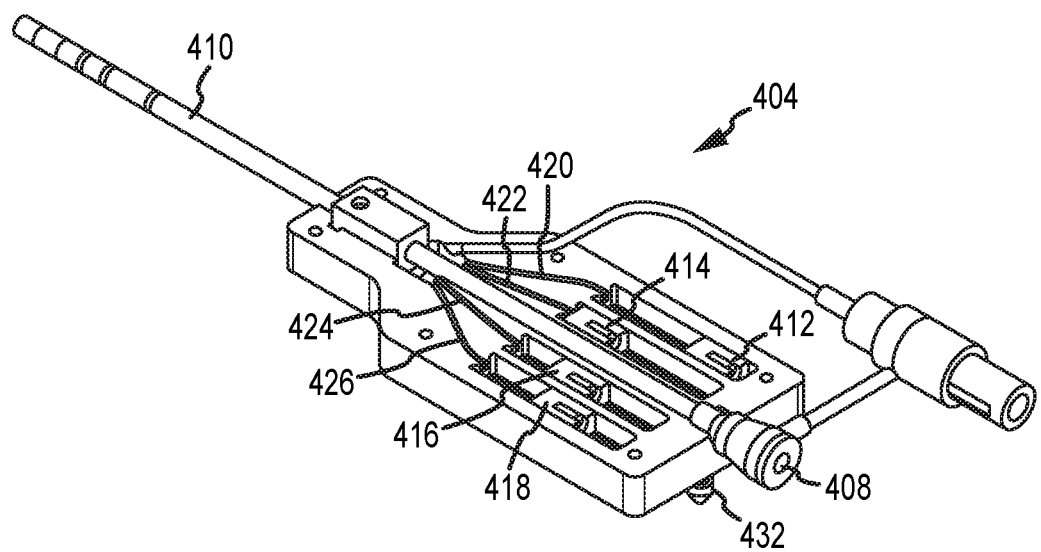

In the Figures to follow, FIGS. 20A-20B will show a manipulator assembly, FIGS. 21A-21C will show a manipulation base, and FIGS. 22A-22B will show a device cartridge.

FIG. 20A is an isometric view, with portions omitted for clarity, of manipulator assembly 302. Assembly 302 includes a catheter manipulator mechanism 304, a sheath manipulator mechanism 306, a catheter manipulation base 308, a sheath manipulation base 310, a first (catheter) drive mechanism 312, a second (sheath) drive mechanism 314, and a track 356. As further shown, assembly 302 further includes a catheter cartridge 402 and a sheath cartridge 404, with a catheter 406 having a proximal end opening 408 coupled to the catheter cartridge 402 and a sheath 410 coupled to the sheath cartridge 404.

Catheter and sheath manipulator mechanisms 304, 306 are configured to manipulate the several different movements of the catheter 406 and the sheath 410. First, each mechanism 304, 306 is configured to impart translation movement to the catheter 406 and the sheath 410. Translation movement here refers to the independent advancement and retraction (withdrawal) as shown generally in the directions designated D1 and D2 in FIG. 20A. Second, each mechanism 304, 306 is also configured to effect deflection of the distal end of either or both of the catheter and sheath 406, 410. Third, each mechanism 304, 306 can be operative to effect a so-called virtual (omni-directional) rotation of the distal end portion of the catheter 406 and the sheath 410. Virtual rotation can be made through the use of independent four-wire steering control for each device (e.g., eight total steering wires, comprising four sheath control wires and four catheter control wires). The distal end movement is referred to as "virtual" rotation because the outer surface of the sheath (or catheter) does not in fact rotate in the conventional sense (i.e., about a longitudinal axis) but rather achieves the same movements as conventional uni-planar deflection coupled with axial rotation. In addition to the present description of virtual rotation, further details can be found in international application no. PCT/US2009/038597, published 1 Oct. 2009, as WO 2009/120982, which is hereby incorporated by reference as though fully set forth herein.

Each manipulator mechanism 304, 306 further includes a respective manipulation base 308, 310 onto which are received catheter and sheath cartridges 402, 404. Each interlocking base 308, 310 can be capable of travel in the longitudinal direction of the catheter/sheath (i.e., D1, D2 respectively) along a track 356. In an embodiment, D1 and D2 can each represent a translation of approximately 8 linear inches. Each interlocking base 308, 310 can be translated by a respective high precision drive mechanism 312, 314. Such drive mechanisms can include, for example and without limitation, an electric motor driven lead screw or ball screw.

The manipulator mechanisms 304, 306 are aligned with each other such that catheter 406 can pass through sheath 410 in a coaxial arrangement. Thus, sheath 410 can include a water-tight proximal sheath opening 408. Overall, the manipulator mechanisms 304, 306 are configured to allow not only coordinated movement but also relative movement between catheter and sheath cartridges 402, 404 (and thus relative movement between catheter and sheath).

FIG. 20B is an isometric view of manipulator assembly 302, substantially the same as FIG. 20B except that catheter and sheath cartridges 402, 404 are omitted (as well as catheter and sheath 406, 410) so as to reveal an exposed face of the manipulation bases 308, 310.

FIG. 21A is an isometric, enlarged view showing manipulation base 308 (and base 310) in greater detail. Each cartridge 402, 404 has an associated manipulation base 308, 310. Each base 308, 310 can include a plurality of fingers 316, 318, 320 and 322 (e.g., one per steering wire) that extend or protrude upwardly to contact and interact with steering wire slider blocks, such as slider blocks 412, 414, 416, 418 best shown in FIG. 22B, to independently tension select steering wires 420, 422, 424, 426, also best shown in FIG. 22B. Each finger can be configured to be independently actuated (i.e., moved back and forth within the oval slots depicted in FIG. 21A) by a respective precision drive mechanism, such as a motor driven ball screw 324. A plate 326 provides a surface onto which one of the cartridges 402, 404 are seated.

FIG. 21B is an isometric, enlarged view of base 308 (and base 310), substantially the same as FIG. 21A except with plate 326 omitted. Each motor-driven ball screw 324, best shown in FIG. 21A, for both finger control and for cartridge translation control, can further include encoders to measure a relative and/or an absolute position of each element of the system. Moreover, each motor-driven ball screw 324, for both finger control and cartridge translation control, can be outfitted with steering wire force sensors to measure a corresponding steering wire tension. For example, a corresponding finger 316, 318, 320 or 322 can be mounted adjacent to a strain gauge for measuring the corresponding steering wire tension. Each motor-driven ball screw 324 can include a number of components, for example only, a rotary electric motor (e.g., motors 342, 344, 346 and 348), a lead screw 328, a bearing 330 and a coupler 332 mounted relative to and engaging a frame 340. In the depicted embodiments linear actuation is primarily, if not exclusively, employed. However, some known examples of systems with rotary-based device drivers include U.S. application Ser. No. 12/150,110, filed 23 Apr. 2008 (the '110 application); and U.S. application Ser. No. 12/032,639, filed 15 Feb. 2008 (the '639 application). The '110 application and the '639 application are hereby incorporated by reference in their entirety as though fully set forth herein. These and other types of remote actuation can directly benefit from the teaching of the instant disclosure.

FIG. 21C is an isometric, enlarged view of base 308 (and base 310) that is taken from an opposite side as compared to FIGS. 21A-21B. Bases 308, 310 can include components such as a plurality of electrically-operated motors 342, 344, 346 and 348, respectively coupled to fingers 316, 318, 320 and 322. A bearing 354 can be provided to facilitate the sliding of bases 308, 310 on and along track 356. A plurality of inductive sensors (e.g. home sensors) 358 can also be provided for guiding each manipulation base to a home position.

FIG. 22A is an isometric, enlarged view showing, in greater detail, sheath cartridge 404. It should be understood that the description of sheath cartridge 404, except as otherwise stated, applies equally to catheter cartridge 402. Catheter 406 and sheath 410 can be substantially connected or affixed to respective cartridges 402, 404 (e.g., in the neck portion). Thus, advancement of cartridge 404 correspondingly advances the sheath 410 and retraction of cartridge 404 retracts the sheath 410. Likewise, although not shown, advancement of cartridge 402 correspondingly advances catheter 406 while a retraction of cartridge 402 retracts catheter 406. As shown, sheath cartridge 404 includes upper and lower cartridge sections 428, 430.

FIG. 22B is an isometric, enlarged view showing, in greater detail, sheath cartridge 404, with upper section 428 omitted to reveal interior components. Cartridge 404 can include slider blocks (e.g., as shown for cartridge 404, slider blocks 412, 414, 416, 418), each rigidly and independently coupled to a respective one of a plurality of steering wires (e.g., sheath steering wires 420, 422, 424, 426) in a manner that permits independent tensioning of each steering wire. Likewise, cartridge 402 for catheter 406 also includes slider blocks for coupling to a plurality (e.g., four) steering wires. Device cartridges 402, 404 can be provided as a disposable item that is capable of being easily positioned (e.g., snapped) into place onto a respective base 408, 410. Sheath cartridge 404 can be designed in a similar manner as the catheter cartridge 402, but will typically be configured to provide for the passage of catheter 406.

Referring to FIGS. 21A and 22A, catheter and sheath cartridges 402, 404 are configured to be secured or locked down onto respective manipulation bases 308, 310. To couple cartridge 402 (and 404) with base 308 (and 310), one or more locking pins (e.g., 432 in FIG. 22A) on the cartridge can engage one or more mating recesses 360 in the base (see FIG. 21A). In an embodiment, such recesses 360 can include an interference lock such as a spring detent or other locking means. In an embodiment, such other locking means can include a physical interference that can require affirmative/positive action by the user to release the cartridge. Such action can include or require actuation of a release lever 362. Additionally, the cartridge can include one or more locator pins (not shown) configured to passively fit into mating holes on the base (e.g., 364 in FIG. 21A).

In operation, a user first manually positions catheter 406 and sheath 410 (with catheter 406 inserted in sheath 410) within the vasculature of a patient. Once the medical devices are roughly positioned in relation to the heart or other anatomical site of interest, the user can then engage or connect (e.g., "snap-in") the catheter and sheath cartridges into place on respective bases 308, 310. When a cartridge is interconnected with a base, the fingers fit into the recesses formed in the slider blocks. For example, with respect to the sheath cartridge 404 and sheath base 310, each of the plurality of fingers 316, 318, 320 or 322 fit into corresponding recesses formed between the distal edge of slider blocks 412, 414, 416, 418 and a lower portion of the cartridge housing (best shown in FIG. 22B). Each finger can be designed to be actuated in a proximal direction to respectively move each slider block, thereby placing the respective steering wire in tension (i.e., a "pull" wire). Translation, distal end bending and virtual rotation can be accomplished through the use of the RCGS 210.

Figure 23:
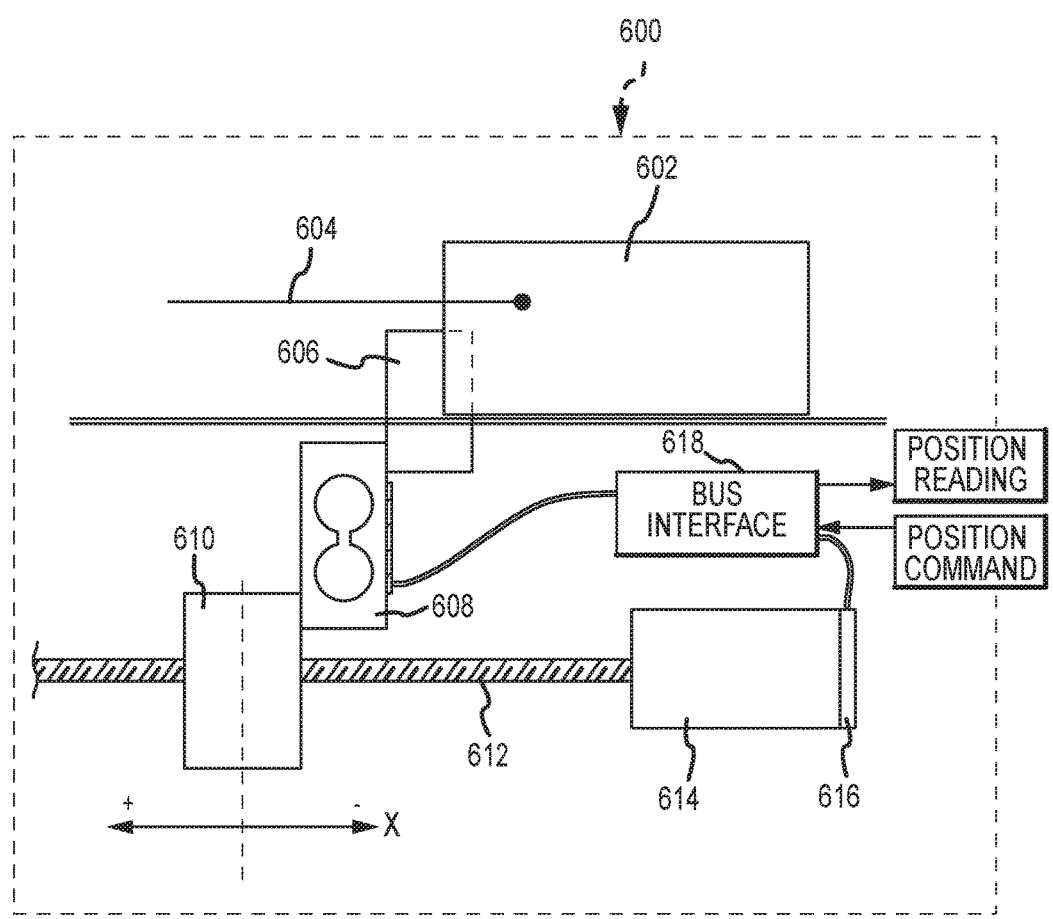
FIG. 23 is a diagrammatic and block diagram view of the sheath manipulation mechanism of FIG. 19.

FIG. 23 is a diagrammatic view of a node suitable for connection to a communications bus (not shown) in RCGS 210. The node includes an actuation unit 600, similar to the actuation mechanisms described above (e.g., catheter actuation mechanism 304). In an embodiment, the RCGS 210 can have at least ten such actuation units (i.e., one for each of the four catheter steering wires, four sheath steering wires, one catheter manipulation base and one sheath manipulation base), which as described include electric motors. Of course, as described above, when the RCGS 210 is configured to manipulate multiple medical devices, each medical device will include a respective actuation assembly, suited to the type of medical device.

FIG. 23 shows in diagrammatic or block form many of the components described above—where appropriate, references to the earlier describe components will be made. Actuation unit 600 includes a first, slidable control member 602 (e.g., the slider as described above) that is connected to or coupled with a second, tensile control member 604 (e.g., the steering wire as described above). The slider 602 can be configured to interface with a third, movable control member 606 (e.g., the finger as described above). The finger 606 can further be operatively coupled with a portion of a sensor 608 (e.g., a force sensor), which, in turn, can be coupled with a translatable drive element 610 that can be mechanically moved. For example, without limitation, translatable drive element 610 can ride on or can otherwise be mechanically moved by a mechanical movement device 612 that, in turn, can be coupled with an electric motor 614. The mechanical movement device 612 can comprise a lead screw while the translatable drive element 610 can comprise a threaded nut, which can be controllably translated by screw 612 in the X+ or X− directions. In another embodiment, mechanical movement device 612 can include a ball screw, while translatable drive element 610 can include a ball assembly. Many variations are possible, as will be appreciated by one of ordinary skill in the art.

The actuation unit 600 also includes a rotary motor position encoder 616 that is coupled to the motor 614 and is configured to output a signal indicative of the position of the motor 614. The encoder 616 can comprise an internal, optical encoder assembly, integral with motor 614, configured to produce a relatively high accuracy output. The motor position sensor can operate in either absolute or relative coordinates. In an embodiment, a second motor position sensor (not shown) can also be provided, such as a potentiometer (or impedance-based), configured to provide a varying voltage output proportional to the motor's rotary position. The output of the secondary position sensor can be used as an integrity check of the operating performance of the primary position sensor (encoder) during start-up or initialization of the actuation unit.

Actuation unit 600 also includes one or more local controllers including a bus interface 618 to facilitate exchange of information between actuation unit 600 and electronic control system 226 (via the bus). The controller communicates with the main electronic control system 226 via the bus interface and is configured, among other things, to (1) receive and execute motor actuation commands issued by the electronic control system 226 for controlling the movements of motor 614; and (2) receive and execute a command (issued by the electronic control system 226) to take a motor position sensor reading, for example, from encoder 616 and subsequently report the reading to system 226.

In accordance with another embodiment, an article of manufacture includes a computer storage medium having a computer program encoded thereon, where the computer program includes code for acquiring or capturing motion of a user and generating corresponding output data, for recognizing a user gesture based on the user motion output data, and for translating the recognized user gesture into one or more commands for an EP diagnostic and/or therapeutic system, including at least a robotic catheter control command, or an electro-anatomic system command. Such embodiments may be configured to execute one or more processors, multiple processors that are integrated into a single system or are distributed over and connected together through a communications network, and where the network may be wired or wireless.

It should be understood that while the foregoing description describes various embodiments of a bedside interface device in the context of the practice of electrophysiology, and specifically catheterization, the teachings are not so limited and can be applied to other clinical settings.

It should be understood that the an electronic control unit as described above may include conventional processing apparatus known in the art, capable of executing pre-programmed instructions stored in an associated memory, all performing in accordance with the functionality described herein. It is contemplated that the methods described herein may be programmed, with the resulting software being stored in an associated memory and where so described, may also constitute the means for performing such methods. Implementation of an embodiment of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A system for enabling a user to remotely control a robotic medical device system, comprising:
   a motion capture apparatus configured to capture motion of a user in a sensing volume and generate output data indicative of the captured user motion, wherein said output data includes fiducial point tracking data associated with a plurality of fiducial points;
   an electronic control unit including a processor and a memory;
   gesture recognition logic stored in said memory and configured to execute on said processor, said gesture recognition logic being configured to recognize a user gesture based on said output data from said motion capture apparatus, said gesture recognition logic being configured to compare a time-based motion of the fiducial points with a plurality of predefined gestures and to output the recognized user gesture when the time-based motion matches one of the plurality of gestures wherein said time-based motion of fiducial points comprises at least a sequence of time-based positions traversed by the fiducial points over a plurality of times; and
   interpreter logic stored in said memory and configured to execute said processor, said interpreter logic being configured to translate the user gesture to a corresponding robotic medical device control command, said command being configured to control an aspect of the operation of the robotic medical device system that includes a medical device and a manipulator assembly including at least one electrically-operated actuation unit configured for one of translation, deflection and rotation of the medical device, said electronic control unit being configured to communicate said command to the robotic medical device system.

2. The system of claim 1 wherein said motion capture apparatus comprises one of (i) a spatially detected glove configured to be worn by the user; (ii) a spatially detected wand configured to be moved by the user; (iii) a spatially detected finger instrument configured to be worn on a finger of the user; (iv) a spatially detected stylus configured to be moved by the user; (v) an optical-based position tracking product; (vi) a magnetic field-based position tracking product; and (vii) a haptic glove configured to be worn by the user configured to capture said user motion.

3. The system of claim 2 wherein said spatially detected glove and stylus are configured to be locatable in three-dimensional space through the use of an optical-based, magnetic field-based, and electrostatic field-based positioning system.

4. The system of claim 2 wherein said haptic glove is configured to detect relative bending of fingers and joints within the hand of the user.

5. The system of claim 1 wherein said plurality of fiducial points are defined with respect to the user, and wherein said fiducial point tracking data includes, for each fiducial point, a respective position, wherein each position includes a respective three-dimensional coordinate in a reference coordinate system, and wherein said fiducial point tracking data further includes, for each fiducial point, a respective time-based plurality of positions.

6. The system of claim 5 wherein said gesture recognition logic is further configured to:

identify a start pose based on said fiducial point tracking data; and record the time-based motion of fiducial points being tracked after the start pose until an end pose is identified based on said fiducial point tracking data.

7. The system of claim 5 wherein a characteristic associated said robotic medical device control command is a commanded magnitude associated with an action involving one of a catheter and a sheath under control of the robotic medical device system, and wherein the commanded magnitude corresponds to a distance between preselected fiducial points.

8. The system of claim 5 wherein a characteristic associated with the robotic medical device control command is a commanded rotation associated with an action involving one of a catheter and a sheath under control of the robotic medical device system, and wherein the commanded rotation corresponds to a rotation angle through which a preselected fiducial point is rotated during the user gesture.

9. The system of claim 1 further comprising a user-actuatable switch coupled to said electronic control unit and having a normally open state, and a user-actuatable closed state, wherein said electronic control unit is configured to disable said communication of said command to the robotic medical device system unless said switch is in said closed state.

10. The system of claim 1 wherein said interpreter logic is further configured to selectively translate, based on a state of context switch parameter, the user gesture into one of (i) the robotic medical device control command configured to control an aspect of the operation of the robotic medical device system and (ii) a mapping control command configured to control an aspect of an electro-anatomic mapping system.

11. The system of claim 10 wherein the sensing volume includes a context switching portion, said system for enabling the user to remotely control further comprising context switching logic stored in said memory and configured for execution by said processor and configured to detect a predetermined context switching gesture based on said output data from said motion capture apparatus originating with user-motion occurring in the context switching portion of the sensing volume.

12. The system of claim 1 wherein said motion capture apparatus comprises an optical sub-system configured to optically detect the motion of the user in the sensing volume.

13. The system of claim 1 wherein the medical device comprises one of a catheter and a sheath.

14. A system for enabling a user to remotely control a robotic medical device system, comprising:

motion capture means for capturing motion of a user in a sensing volume and generating output data indicative of the captured user motion, wherein said output data includes fiducial point tracking data associated with a plurality of fiducial points;

gesture recognition means for recognizing a user gesture based on said output data from said motion capture means, said gesture recognition means being configured to compare a time-based motion of the fiducial points with a plurality of predefined gestures and to output the recognized user gesture when the time-based motion matches one of the plurality of gestures wherein said time-based motion of fiducial points comprises at least a sequence of time-based positions traversed by the fiducial points over a plurality of times;

interpreter means for translating the user gesture to a corresponding robotic medical device control command wherein said command is configured to control an aspect of the operation of the robotic medical device system that includes a medical device and a manipulator assembly including at least one electrically-operated actuation unit configured for one of translation, deflection and rotation of the medical device; and communication means for communicating said command to the robotic medical device system.

15. The system of claim 14 wherein said motion capture apparatus comprises one of (i) a spatially detected glove configured to be worn by the user; (ii) a spatially detected wand configured to be moved by the user; (iii) a spatially detected finger instrument configured to be worn on a finger of the user; (iv) a spatially detected stylus configured to be moved by the user; (v) an optical-based position tracking product; (vi) a magnetic field-based position tracking product; and (vii) a haptic glove configured to be worn by the user configured to capture said user motion.

16. The system of claim 15 wherein said spatially detected glove and stylus are configured to be locatable in three-dimensional space through the use of an optical-based, magnetic field-based, and electrostatic field-based positioning system.

17. The system of claim 15 wherein said haptic glove is configured to detect relative bending of fingers and joints within the hand of the user.

18. The system of claim 14 wherein said plurality of fiducial points are defined with respect to the user, and wherein said fiducial point tracking data includes, for each fiducial point, a respective position, wherein each position includes a respective three-dimensional coordinate in a reference coordinate system, and wherein said fiducial point tracking data further includes, for each fiducial point, a respective time-based plurality of positions.

19. The system of claim 18 wherein said gesture recognition means is further configured for:

identifying a start pose based on said fiducial point tracking data; and recording the time-based motion of fiducial points being tracked after the start pose until an end pose is identified based on said fiducial point tracking data.

* * * * *